(12) United States Patent
Kim et al.

(10) Patent No.: US 10,888,839 B2
(45) Date of Patent: Jan. 12, 2021

(54) AVERAGE-DENSITY-ADJUSTABLE STRUCTURE, AND MATERIAL CHANGE AND SELECTIVE BONDING PROCESS USING SAME

(71) Applicant: KOREA UNIVERSITY RESEARCH AND BUSINESS FOUNDATION, Seoul (KR)

(72) Inventors: Jung Bae Kim, Seoul (KR); Ju Sang Yang, Seoul (KR); In Seon Lee, Gyeonggi-do (KR); Han Sol Kim, Gyeonggi-do (KR); Jong Seong Yim, Chungcheongnam-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 58 days.

(21) Appl. No.: 15/739,445

(22) PCT Filed: Jun. 27, 2016

(86) PCT No.: PCT/KR2016/006864
§ 371 (c)(1),
(2) Date: Dec. 22, 2017

(87) PCT Pub. No.: WO2016/209063
PCT Pub. Date: Dec. 29, 2016

(65) Prior Publication Data
US 2018/0185818 A1     Jul. 5, 2018

(30) Foreign Application Priority Data

Jun. 25, 2015  (KR) .................. 10-2015-0090710
Jun. 26, 2015  (KR) .................. 10-2015-0091304
(Continued)

(51) Int. Cl.
*C12M 1/09*     (2006.01)
*B01D 15/00*    (2006.01)
(Continued)

(52) U.S. Cl.
CPC ............ *B01J 20/261* (2013.01); *B01D 15/00* (2013.01); *B01D 53/02* (2013.01); *B01D 53/86* (2013.01);
(Continued)

(58) Field of Classification Search
CPC .......... C02F 1/281; C02F 1/285; C02F 11/02; C02F 1/288; C02F 3/06; C02F 3/10;
(Continued)

(56) References Cited

U.S. PATENT DOCUMENTS 5,316,671 A * 5/1994 Murphy ............. B01D 21/0018
                                                    210/121
5,507,950 A * 4/1996 Senda ...................... C02F 3/06
                                                    210/150
(Continued)

FOREIGN PATENT DOCUMENTS

JP       2013-504442 A    2/2013
KR    10-2009-0077024 A    7/2009
(Continued)

OTHER PUBLICATIONS

Kim, J., et al., "Nanobiocatalysis and its potential applications", "Trends in Biotechnology", Sep. 18, 2008, pp. 639-646, vol. 26, No. 11.
(Continued)

*Primary Examiner* — Claire A Norris
(74) *Attorney, Agent, or Firm* — Hultquist, PLLC; Steven J. Hultquist

(57) ABSTRACT

The present invention relates to an average-density-adjustable structure and more specifically provides a structure the
(Continued)

average density of which is adjusted by changing the material of the structure and the size of a void formed therein and which can thereby float on the surface of or in a liquid and can easily bond with or change a material present in a gas or liquid by being equipped with a first material, which is one among an organic catalyst, an inorganic catalyst, a microorganism, and a biomolecule.

11 Claims, 14 Drawing Sheets

(30) Foreign Application Priority Data

Jun. 26, 2015 (KR) ........................ 10-2015-0091306
May 30, 2016 (KR) ........................ 10-2016-0066412

(51) Int. Cl.
| | | |
|---|---|---|
| *B01J 20/26* | (2006.01) | |
| *B01J 20/28* | (2006.01) | |
| *B01J 20/32* | (2006.01) | |
| *B01J 31/00* | (2006.01) | |
| *B01D 53/86* | (2006.01) | |
| *C02F 3/34* | (2006.01) | |
| *B01D 53/02* | (2006.01) | |
| *C12N 11/08* | (2020.01) | |
| *C02F 103/08* | (2006.01) | |

(52) U.S. Cl.
CPC ... *B01J 20/28011* (2013.01); *B01J 20/28042* (2013.01); *B01J 20/28097* (2013.01); *B01J 20/321* (2013.01); *B01J 20/3204* (2013.01); *B01J 20/3221* (2013.01); *B01J 20/3223* (2013.01); *B01J 20/3282* (2013.01); *B01J 31/003* (2013.01); *C02F 3/343* (2013.01); *C12M 23/56* (2013.01); *C12N 11/08* (2013.01); *B01D 2253/30* (2013.01); *B01D 2255/804* (2013.01); *B01D 2255/90* (2013.01); *B01D 2257/504* (2013.01); *B01D 2257/91* (2013.01); *B01J 2220/46* (2013.01); *B01J 2220/4812* (2013.01); *C02F 2103/08* (2013.01)

(58) Field of Classification Search
CPC ........... B01J 20/28011; B01J 20/261; B01J 20/28042; B01J 20/28097; B01J 20/3204; B01J 20/321; B01J 20/3221; B01J 20/3223; B01J 20/3282; B01J 31/003; B01D 15/00; B01D 53/02; B01D 53/86; C12M 23/56; C12N 11/08
USPC .......................................... 210/242.1, 170.05
See application file for complete search history.

(56) References Cited

U.S. PATENT DOCUMENTS

| | | | | |
|---|---|---|---|---|
| 6,273,402 | B1 * | 8/2001 | Cheng | B01F 3/04609 |
| | | | | 210/242.2 |
| 6,344,144 | B1 * | 2/2002 | Long | B01F 3/04106 |
| | | | | 210/170.05 |
| 7,198,941 | B2 * | 4/2007 | Fadnavis | C12M 21/18 |
| | | | | 210/291 |
| 2005/0005869 | A1 * | 1/2005 | Fritter | A01K 1/0152 |
| | | | | 119/173 |
| 2014/0378926 | A1 * | 12/2014 | Ota | A61F 13/5323 |
| | | | | 604/367 |
| 2016/0221853 | A1 * | 8/2016 | Cort | C02F 11/121 |

FOREIGN PATENT DOCUMENTS

| | | |
|---|---|---|
| KR | 10-2012-0009474 A | 1/2012 |
| KR | 10-2014-0019189 A | 2/2014 |

OTHER PUBLICATIONS

Rethwisch, D. G., et al., "Enzyme-Facilitated Transport and Separation of Organic Acids through Liquid Membranes", "Journal of the American Chemical Society", Feb. 1, 1990, pp. 1649-1650, vol. 112, No. 4.

* cited by examiner

AVERAGE-DENSITY-ADJUSTABLE STRUCTURE, AND MATERIAL CHANGE AND SELECTIVE BONDING PROCESS USING SAME

CROSS-REFERENCE TO RELATED APPLICATIONS

This application is a U.S. national phase under the provisions of 35 U.S.C. § 371 of International Patent Application No. PCT/KR2016/006864 filed Jun. 27, 2016, which in turn claims priority of: Korean Patent Application No. 10-2015-0090710 filed Jun. 25, 2015, Korean Patent Application No. 10-2015-0091304 filed Jun. 26, 2015, Korean Patent Application No. 10-2015-0091306 filed Jun. 26, 2015, and Korean Patent Application No. 10-2016-0066412 filed May 30, 2016. The disclosures of such international patent application and Korean priority patent applications are hereby incorporated herein by reference in their respective entireties, for all purposes.

TECHNICAL FIELD

The present invention relates to an average-density-adjustable structure, and particularly, to a structure whose average density is adjusted by changing the material of the structure and the size of a void formed therein so that the structure can float on a surface of a liquid or be suspended in a liquid or a composite structure including the structure can be positioned at an interface between a gas and a liquid or between a liquid and a liquid, wherein the composite structure includes a first material, which is one of an organic catalyst, an inorganic catalyst, a microorganism, and a biomolecule so that the structure can easily combine with or convert a material present in a gas or liquid.

BACKGROUND ART

Reactions which proceed at interfaces between a gas and a liquid and between a liquid and a liquid play an important role in various fields such as collection and application of carbon dioxide, bioconversion, removal of a suspended pollutant such as oil, and the like.

For example, in order to convert carbon dioxide in the atmosphere and apply the converted carbon dioxide to culture microalgae, the technology in which an open pond-type incubator is installed on at least a laboratory scale to a several hundred hectare-scale and microalgae grows in the incubator has been conventionally proposed. Carbon dioxide in the atmosphere is dissolved in a liquid included in the incubator and thus converted into bicarbonate ions, and the bicarbonate ions may be applied as a nutrient for culturing microalgae. However, since it takes a considerably long time for carbon dioxide in the atmosphere to be naturally dissolved in a liquid, a substantial effect of reducing carbon dioxide is insignificant, and effective cultivation of microalgae is difficult.

In addition, since the concentration of carbon dioxide in the atmosphere is 400 ppm, which is very low, there is a problem in that an amount of carbon dioxide is too small to convert carbon dioxide in the atmosphere into useful byproducts such as bicarbonate ions without an additional catalytic action.

Recently, the technology in which carbon dioxide is converted at a significantly high rate by adding a carbonic anhydrase, which is an organic catalyst theoretically capable of converting one-million carbon dioxide molecules into bicarbonate ions per second, to a liquid, and the microalgae culture rate and carbonate synthesis rate are significantly promoted by applying the converted bicarbonate ions as a nutrient for culturing microalgae or a raw material for synthesizing a carbonate, thereby an effect of reducing carbon dioxide is improved has been proposed.

However, in such a catalytic reaction at interfaces, most of the catalytic material uniformly dispersed in a liquid is not used, and only some of the catalytic material present at an interface between a gas and a liquid or between a liquid and a liquid is involved in the reaction, thereby efficiency may decrease.

Therefore, in order to effectively apply a catalytic material to the reaction at an interface, there is an urgent need for development of a suspended structure which may be positioned at an interface between a gas and a liquid or between a liquid and a liquid, may include a catalytic material so as to easily combine with or convert a material present in a gas or liquid, and may protect a catalytic material from a change in environment for a long period of time.

In addition, there has been disclosed a bead-type structure which may be applied to a catalytic reaction at an interface between a gas and a liquid or in a liquid.

However, since it is not possible to adjust the buoyancy of a conventional bead-type structure due to characteristics of the individual liquid used in the reaction, the following problems may arise.

Specifically, when there is a flow of a liquid, a conventional bead-type structure does not exhibit sufficient buoyancy, and thus may settle in a reaction container. In this case, when a reactor includes a product outlet pipe in a lower part thereof, a bead-type structure may be discharged.

In addition, in the reaction which proceeds at an interface between a gas and a liquid, when the liquid has a low density, a conventional bead-type structure does not exhibit sufficient buoyancy, and thus may settle at a bottom of a reaction container or positioned in the liquid, thereby the structure may not be involved in the reaction.

Additionally, in a reactor in which an overflow occurs, when a conventional bead-type structure is suspended at an interface between a gas and a liquid, the structure may be discharged to the outside.

DISCLOSURE

Technical Problem

It is an aspect of the present invention to provide an average density-adjustable structure, more particularly, a structure whose average density can be adjusted by changing the material of the structure and the size of a void formed therein so that the structure can float on a surface of a liquid or be suspended in a liquid, and which includes an organic catalyst, an inorganic catalyst, a microorganism, and a biomolecule so that the structure can easily combine with or convert a material present in a gas or liquid.

In addition, it is another aspect of the present invention to provide a structure which can be positioned at an interface between a gas and a liquid, can easily combine with or convert a material present in a gas or liquid by including a reactant, and can protect a catalytic material from a change in environment for a long period of time.

Additionally, it is still another aspect of the present invention to provide a structure which can be positioned at an interface between a liquid and a liquid, and a process of converting a reactant which can significantly improve the conversion rate of reactants at an interface between a liquid and a liquid by introducing the structure which may be positioned at the interface and including a first material in the structure.

In addition, the structure may be applied to convert a carbonate and promote the growth of microalgae by collecting carbon dioxide using the structure, to purify a liquid by decomposing oil present in the liquid, or to antifouling for preventing and removing microorganism contamination.

Technical Solution

In order to accomplish the above objectives, according to an embodiment of the present invention, there is provided a structure which includes a body whose density is adjustable and whose position is accordingly adjustable in such a way that the body floats on a surface of a liquid or settles in a liquid; and a first material included in the body.

The density of the body may be adjusted in accordance with a material of the body or a size of a void formed therein.

The body may include at least one support including the first material and at least one density-adjusting body coupled to one end of the support.

The support may have at least one platy structure having a mesh form.

The body may include at least one void formed therein, the void may be filled with a second material, and the second material may include one or more materials selected from the group consisting of air, nitrogen, oxygen, argon, carbon dioxide, neon, ozone, helium, methane, xenon, krypton, and hydrogen.

The body may include at least one selected from acrylonitrile butadiene styrene, polythiophene, polylactic acid, polyvinyl alcohol, polycaprolactam, polycaprolactone, poly(lactic-co-glycolic acid), polyacrylonitrile, polyester, polyethylene, polyethyleneimine, polypropylene oxide, polyurethane, polyglycolic acid, polyethylene terephthalate, poly(methyl methacrylate), polystyrene, polydimethylsiloxane, poly(styrene-co-maleic anhydride), Teflon, collagen, nylon, cellulose, chitosan, glass, gold, silver, aluminum, iron, copper, and silicon.

The first material may be combined with the body by adsorption, ionic bonding, covalent bonding, or an adhesive material.

The first material may be combined with a carrier by adsorption, ionic bonding, covalent bonding, or an adhesive material, and the carrier may be combined with a surface of the body or embedded in the body by adsorption, ionic bonding, covalent bonding, or an adhesive material.

The carrier may include at least one selected from polymer fibers, porous particles, carbon tubes, polymer tubes, wires, pillars, graphene, fullerenes, polynorepinephrine, and spherical particles.

The first material may include at least one selected from an organic catalyst, an inorganic catalyst, a biomolecule, and a microorganism.

The organic catalyst may form an aggregate through cross-linking between organic catalysts using a cross-linking agent, wherein the cross-linking agent may include one or more selected from the group consisting of diisocyanate, dianhydride, diepoxide, dialdehyde, diimide, 1-ethyl-3-dimethylaminopropyl carbodiimide, glutaraldehyde, bis(imidoester), bis(succinimidyl ester), diacid chloride, dopamine, a compound containing a dopamine-derived catechol group, genipin, and ethylene glycol diglycidyl ether.

The organic catalyst may settle through a settling agent, and may form an aggregate through cross-linking between organic catalysts using a cross-linking agent, wherein the cross-linking agent may include one or more selected from the group consisting of diisocyanate, dianhydride, diepoxide, dialdehyde, diimide, 1-ethyl-3-dimethylaminopropyl carbodiimide, glutaraldehyde, bis(imidoester), bis(succinimidyl ester), diacid chloride, dopamine, a compound containing a dopamine-derived catechol group, genipin, and ethylene glycol diglycidyl ether, and the settling agent may include one or more selected from the group consisting of methanol, ethanol, 1-propanol, 2-propanol, butyl alcohol, acetone, polyethylene glycol, ammonium sulfate, sodium chloride, sodium sulfate, sodium phosphate, potassium chloride, potassium sulfate, potassium phosphate, and an aqueous solution thereof.

The organic catalyst may include one or more selected from the group consisting of carbonic anhydrases, glucose oxidases, trypsin, chymotrypsin, subtilisin, papain, thermolysin, lipases, peroxidases, acylases, lactonase, proteases, tyrosinase, laccases, cellulases, xylanases, organophosphohydrolase, cholinesterases, formate dehydrogenases, aldehyde dehydrogenases, alcohol dehydrogenases, glucose dehydrogenases, and glucose isomerase, the inorganic catalyst may include one or more selected from the group consisting of platinum, rhodium, palladium, lead, iridium, rubidium, iron, nickel, zinc, cobalt, copper, manganese, titanium, ruthenium, silver, molybdenum, tungsten, aluminum, antimony, tin, bismuth, barium, osmium, nitrogen oxide, copper oxide, manganese oxide, titanium oxide, vanadium oxide, and zinc oxide, the biomolecule may include one or more selected from the group consisting of albumin, insulin, collagen, an antibody, an antigen, protein A, protein G, avidin, streptavidin, biotin, a nucleic acid, a peptide, a lectin, and a carbohydrate, and the microorganism may include one or more selected from the group consisting of *Bacillus subtilis, Bacillus licheniformis, Bacillus polyfermenticus, Bacillus mesentericus, Saccharomyces cerevisiae, Clostridium butyricum, Streptococcus faecalis, Streptococcus faecium, Micrococcus caseolyticus, Staphylococcus aureus, Lactobacillus casei, Lactobacillus plantarum, Leuconostoc mesenteroides, Debaryomyces nicotianae, Acinetobacter calcoaceticus, Alcaligenes odorans, Aromatoleum aromaticum, Geobacter metallireducens, Dechloromonas aromatic, Arthrobacter* sp., and *Alcanivorax borkumensis*.

According to another embodiment of the present invention, there is provided a process of converting or selectively combining with a reactant, which includes disposing the above-described structure at an interface between a gas and a liquid; and bringing the structure including a first material in contact with a material present in the gas or liquid to convert or combine with the material.

According to still another embodiment of the present invention, there is provided a process of converting or selectively combining with a reactant, which includes disposing the above-described structure at an interface between a liquid and a liquid; and bringing the structure including a first material in contact with a material present in the liquids to convert or combine with the material.

Advantageous Effects

In a density-adjustable structure according to an embodiment of the present invention, an average density of the structure can be easily adjusted by adjusting the material of the structure and the size of a void, and thus the structure can be disposed at various positions in any liquid by adjusting buoyancy.

In addition, since the structure exhibits sufficient buoyancy, it can be disposed in such a way that the structure floats on a surface of a liquid. In this case, although the structure has a small surface area for a reaction, a reaction can stably proceed when there is a flow of the liquid. Also, the structure can be appropriate when a reaction should proceed at interfaces between a gas and a liquid and between a liquid and a liquid. Further, when being positioned in such a way that the structure floats on a surface of a liquid, the structure can be easily recovered after the reaction.

Additionally, in a reaction in which an overflow occurs, a structure, which is designed to exhibit relatively low buoyancy so that the structure is positioned in a liquid or settles at a bottom of a reaction container, is not discharged to the outside of a reaction container even when a reacting fluid overflows. Also, in a reaction in which the structure should have a large surface area for the reaction, when the structure is designed to exhibit appropriate buoyancy to be disposed in a liquid, efficiency can increase. Further, when a reaction container includes a product outlet pipe in a lower part thereof, the structure exhibiting sufficient buoyancy can be provided to prevent introduction into the product.

In addition, since the material of the structure and the size of a void can be sufficiently adjusted, the structure can be widely used in various fields.

One of the structures according to an embodiment of the present invention can include a support having a body formed in a mesh shape and one or more density-adjusting bodies coupled to one end of the support, and allow the support to float at an interface between a gas and a liquid or be suspended at an interface between a liquid and a liquid by adjusting the density of the density-adjusting body.

In addition, the structure includes a protrusion and a coupling groove, and thus the support can be coupled with the density-adjusting body without being separated.

In one of the structures according to an embodiment of the present invention, at least two platy supports can be laminated to support a first material.

The structure according to an embodiment of the present invention can be positioned at an interface between a gas and a liquid, and can include a first material so as to easily combine with or convert a material present in a gas or liquid.

In addition, the structure includes a first material and thus can be applied to collect and apply carbon dioxide, to decompose and remove oil present in a liquid, or to prevent or remove microorganism contamination.

The structure according to an embodiment of the present invention can be positioned at an interface between a liquid and a liquid, prevent a product converted through a reaction at an interface between a liquid and a liquid from being reconverted to a reactant, and significantly improve the yield of a product by disposing a first material at an optimum position.

In addition, the structure can be used to separate and/or recover a material present in a specific liquid at a high concentration. Also, the material can be synthesized through separation of an enantiomer and reactions at an interface.

DESCRIPTION OF DRAWINGS

FIG. 12A is a schematic diagram illustrating a state in which the structure floats on a liquid containing microalgae and is operated, and FIG. 12B is a schematic diagram illustrating a state in which the structure floats on a liquid containing oil and is operated.

MODES OF THE INVENTION

Figure 1:
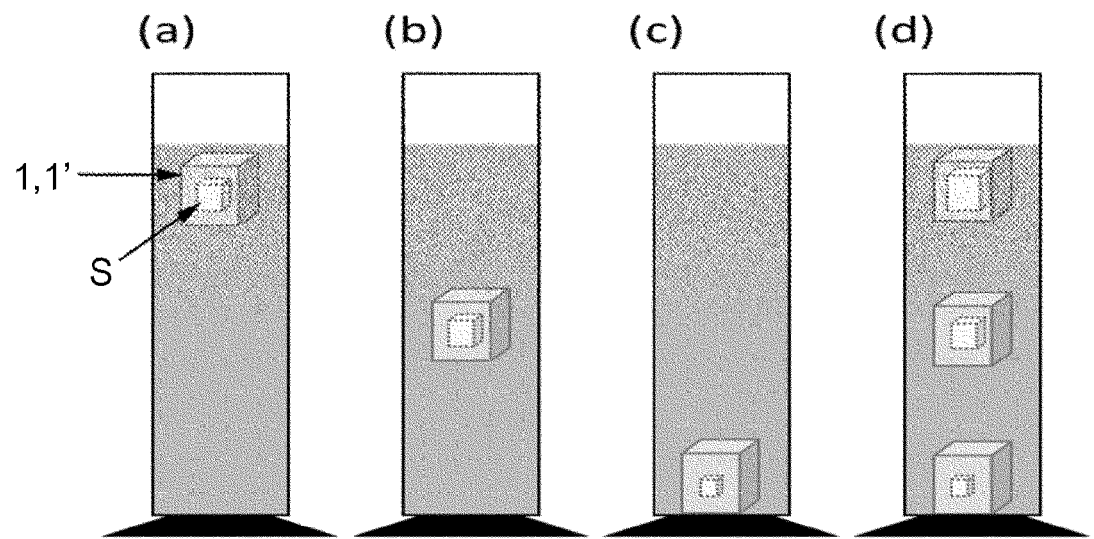
FIG. 1, in panels (a) through (d) thereof, illustrates a first embodiment of a structure according to an embodiment of the present invention and the manner in which it is suspended at varying densities as adjusted by the volume of a void.

Hereinafter, embodiments of the present invention that are easily performed by those skilled in the art will be described in detail with reference to the accompanying drawings. However, embodiments of the present invention may be implemented in several different forms, and are not limited to embodiments described herein. In addition, parts irrelevant to description are omitted in the drawings in order to clearly explain embodiments of the present invention. The same or similar parts are denoted by the same reference numerals throughout this specification.

Figure 2:
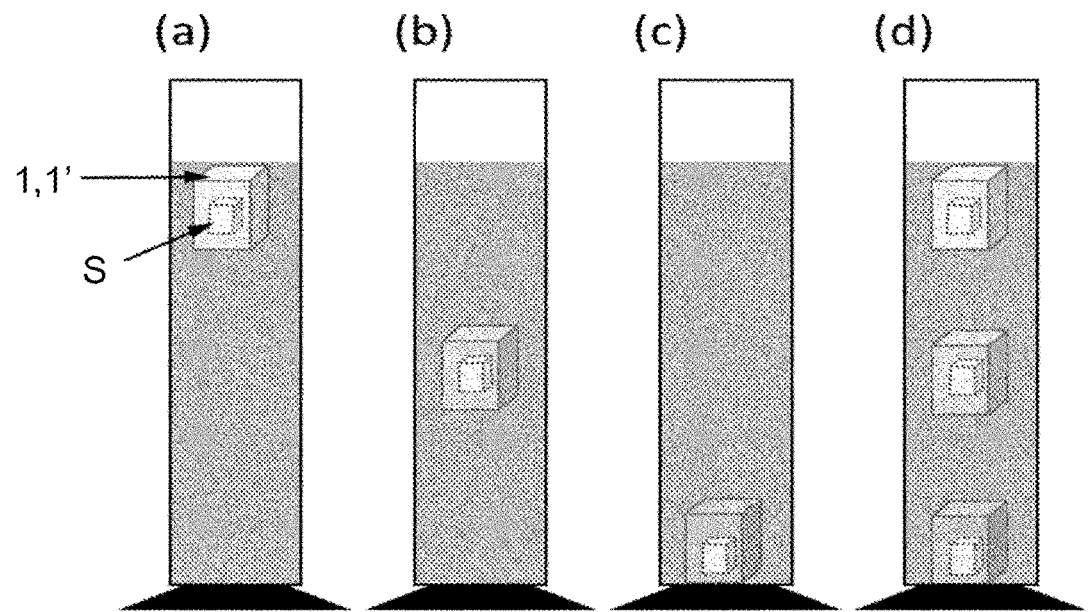
FIG. 2 is a diagram illustrating a first embodiment of a structure according to an embodiment of the present invention and the manner in which it is suspended at varying densities as adjusted by the material of the structure.

Structures 1, 1' according to an embodiment of the present invention may be suspended or sink in a liquid in accordance with an average density of the structure, as shown in FIGS. 1 and 2.

The structure includes a void therein as shown in FIG. 1, wherein the void may accommodate a second material, and an average density of the structure may be adjusted by adjusting the volume of the void.

In addition, the average density of the structure may be adjusted by changing a material of the structure and a composition of the material as shown in FIG. 2.

In this case, the structure is hexahedral, but the present invention is not necessarily limited thereto. The structure may be formed in various shapes as long as it includes a space for accommodating a gas and the space can be closed.

Specifically, referring to FIG. 1, when the sizes and materials of the structures 1, 1' are maintained constant, the manner in which the structures 1, 1' are suspended is dependent on the density as determined by the volume of the void S formed in the structures 1, 1'.

In addition, the void S in a body 10' of the structure 1' may be filled with a second material such as a suspension-adjusting material, and there may be at least one void. That is, there may be a plurality of the voids.

In this case, the buoyancy of the structures 1, 1' may be adjusted by adjusting an amount of the second material in the void.

Here, the second material may include at least one materials selected from air, nitrogen, oxygen, argon, carbon dioxide, neon, ozone, helium, methane, xenon, krypton, and hydrogen.

In order to facilitate the description of the present invention, a case in which the second material is air will be described as an example. The ratio of the volume of air in the void to the entire volume of the structure is denoted as percentage (%). Referring to FIG. 1, panel (a), when the volume percentage of air in the void is 2.8% or more, the structures 1, 1' may be positioned at an upper part of a liquid. Referring to FIG. 1, panel (b), when the volume percentage of air in the void is greater than 2.6 to less than 2.8%, the structure may be positioned at a middle part of a liquid.

In addition, referring to FIG. 1, panel (c), when the volume percentage of air in the void is 0 to 2.6%, the structure may be positioned at a lower part of a liquid.

Therefore, referring to FIG. 1, panel (d), the position of the structure may be adjusted by adjusting an amount of second material in the void, thereby the buoyancy of the structure may be adjusted.

Accordingly, a position at which the structures 1, 1' are suspended in a liquid may be dependent on the volume of the void S and an amount of second material in the void.

Alternatively, referring to FIG. 2, when the sizes of the structures 1, 1' are maintained constant, the manner in which the structure 1, 1' are suspended is dependent on the density as determined by a material of the structure and a composition of the material.

In the adjustment of an average density in accordance with the material of the body 10' of the structure, when the structures 1, 1' are to float on a surface of a liquid, the body 10' may be made of a material having a low average density. On the other hand, when the structures 1, 1' are to be suspended at an interface between a liquid and liquid or in a liquid, the body 10' may be made of a material having a high average density.

In this case, when there is a flow of the liquid, a material of the body and a composition of the material may be selected in such a way that the body has a density that is resistant to flow.

The structures 1, 1' having components as described above may be adjusted in such a way that the structures are suspended at an interface between a gas and a liquid or between a liquid and a liquid or are positioned in a liquid or in a bottom of a liquid. For this purpose, an average density of the structures 1, 1' may be adjusted. In this case, an average density of the structures 1, 1' may be adjusted in accordance with the type and composition of a material or the volume of the void S.

That is, an average density of the bodies of the structures 1, 1' may be adjusted in accordance with a material of the structure and a composition of the material or the volume of the void.

Figure 3:
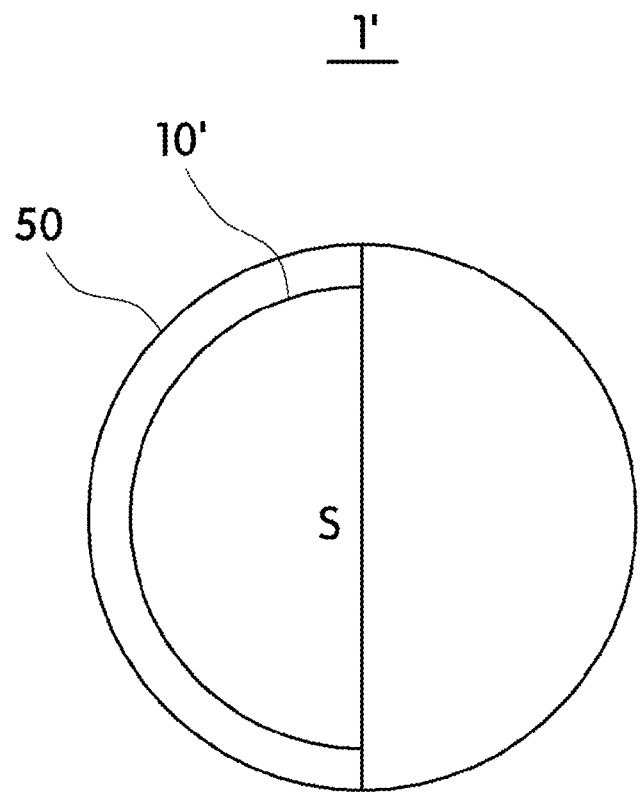
FIG. 3 is a diagram illustrating a first embodiment of a structure according to an embodiment of the present invention.

The structure having characteristics as described above according to an embodiment of the present invention may be made in various shapes. As a first embodiment, the structure may be spherical as shown in FIG. 3, and this is because a spherical shape is most efficient in sufficiently increasing an area for a reaction between a reacting fluid in a liquid and a material immobilized on an outer surface of the body. Also, when the structure is spherical, an area for collision between structures occurring when a plurality of bodies are introduced into a reaction container may be reduced.

However, the body of the structure is not limited to a spherical shape. The structure may be formed in various shapes as long as it includes a space (the void S) for accommodating a reactant and the space can be closed.

The structure 1' having the configuration according to the first embodiment may include a body 10' and a carrier 50 as shown in FIG. 3. A void S into which a reactant is introduced may be formed in the body 10', and various first materials for reacting the reactant in the void with a liquid 5' in a reaction container 7' may be immobilized on an outer surface of the body.

Here, the body 10' may be composed of a material capable of immobilizing various materials. That is, the body 10' should be able to grow various first materials or a carrier on an outer surface.

In addition, the body 10' may include a metal material for preventing the body 10' from being corroded.

Specifically, the body 10' with a reactant is suspended in a liquid 3' in the reaction container 7', and thus may be corroded due to the liquid 3'. Accordingly, in order to prevent the body 10' from being corroded, the body may include a metal material together with the above-described materials.

In addition, the metal material in the body 10' may be stainless steel or the like, but the present invention is not limited thereto. That is, any material may be used as long as it is capable of easily immobilizing the various materials and preventing the body from being corroded at the same time.

The structure 1' having the above-described configuration may be appropriately used in accordance with a structure of the reaction container 7 by adjusting an average density of the structure 1'.

Figure 4:
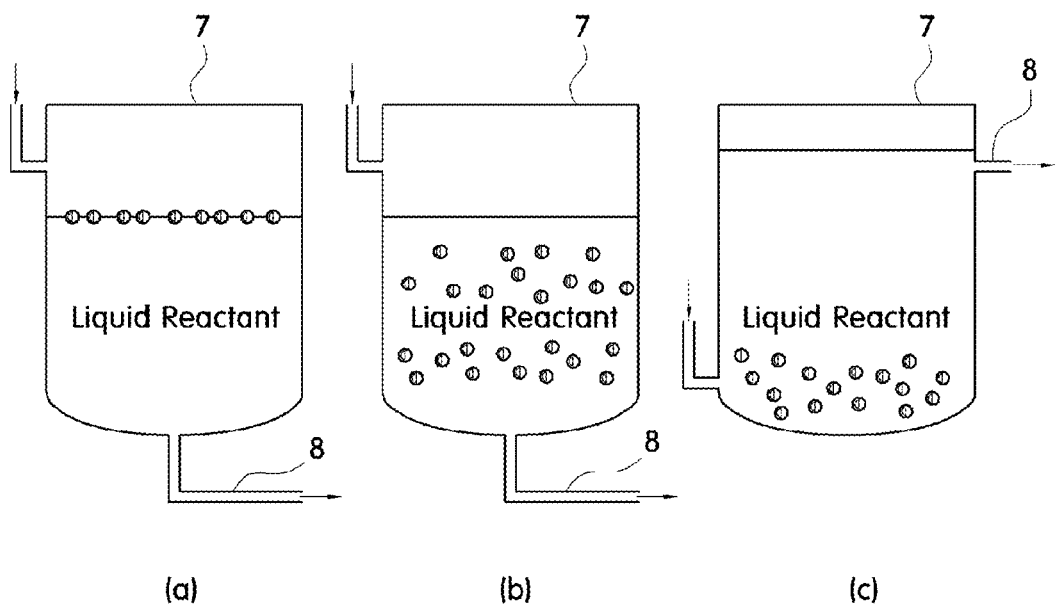
FIG. 4, in panels (a), (b), and (c), illustrates reaction containers used with varying densities of a structure according to an embodiment of the present invention.

As shown in FIG. 4, panels (a) and (b), when a product outlet pipe 8 is connected to a lower part of the reaction container 7, an average density of the structure 1' may be adjusted in such a way that the structure is positioned at an upper part or a boundary of a liquid. In this case, since an average density of the structure 1' is adjusted in such a way that the structure is suspended in a liquid or at a boundary of a liquid, the structure may be prevented from being discharged to the outside through the outlet pipe 8 even when the product is discharged through the outlet pipe 8.

As shown in FIG. 4, panel (c), when the product outlet pipe 8 is connected to an upper part of the reaction container 7, an average density of the structure 1' may be adjusted in such a way that the structure is positioned at a lower part of a liquid. In this case, since the structure is suspended in a liquid by reducing the volume of the void S, the structure 1' may be prevented from being discharged to the outside through the outlet pipe 8 even when an overflow of a product occurs.

Meanwhile, the structure 1' according to the first embodiment of the present invention is shown and described as a structure in which the body is suspended in a liquid, but the present invention is not limited thereto. That is, a floating body for suspending the body in a liquid may be coupled.

Figure 7:
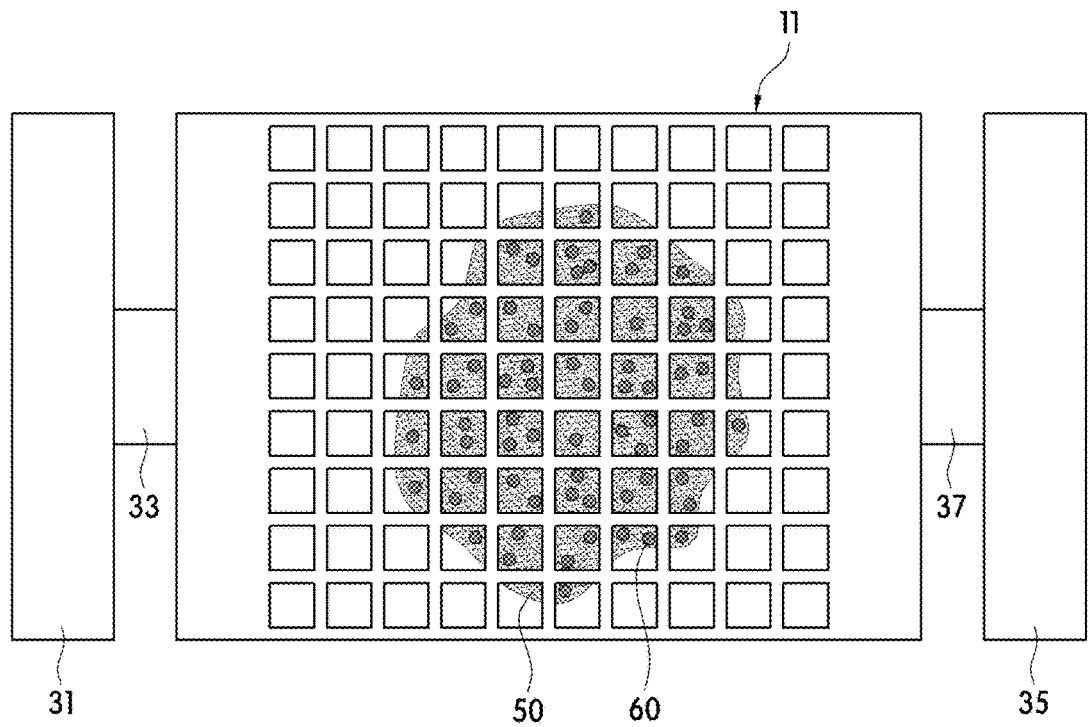
FIG. 7 is a plan view of a structure according to an embodiment of the present invention that illustrates a first material combined with a carrier of the structure.
Figure 8:
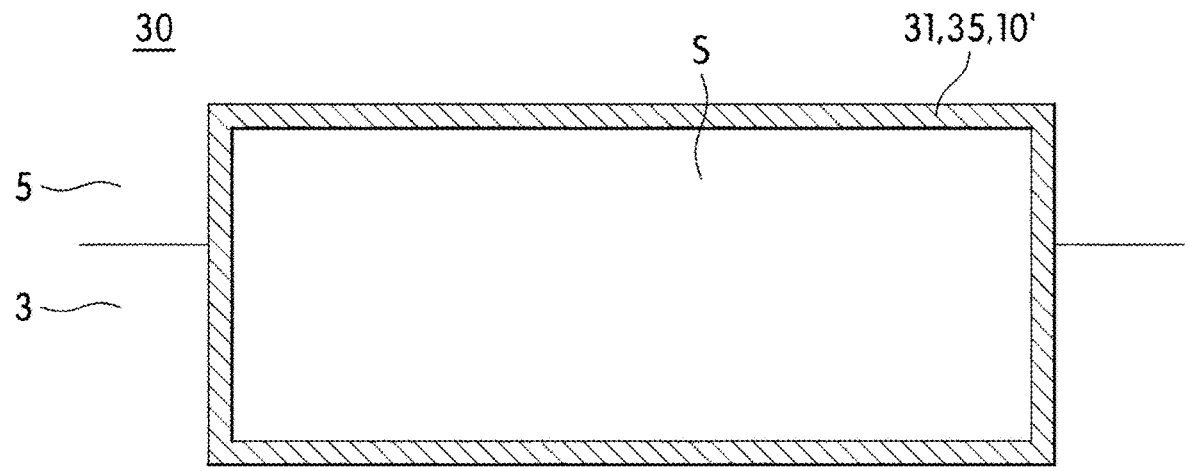
FIGS. 8 to 11 are sectional views of exemplary modifications of a structure according to an embodiment of the present invention.

Specifically, the structure 1 according to a second embodiment of the present invention may include a body and a carrier 50 as shown in FIG. 7. The structure 1 includes the body, and thus may support a first material 60 and may protect the first material from a change in environment for a long period of time.

In addition, the structure 1 may float on a liquid.

For this purpose, the structure 1 may include a support 10 and a density-adjusting body 30. In this case, the density-adjusting body 30 may be coupled to both ends of the support 10, and allows the support 10 to be suspended in a liquid.

Figure 6:
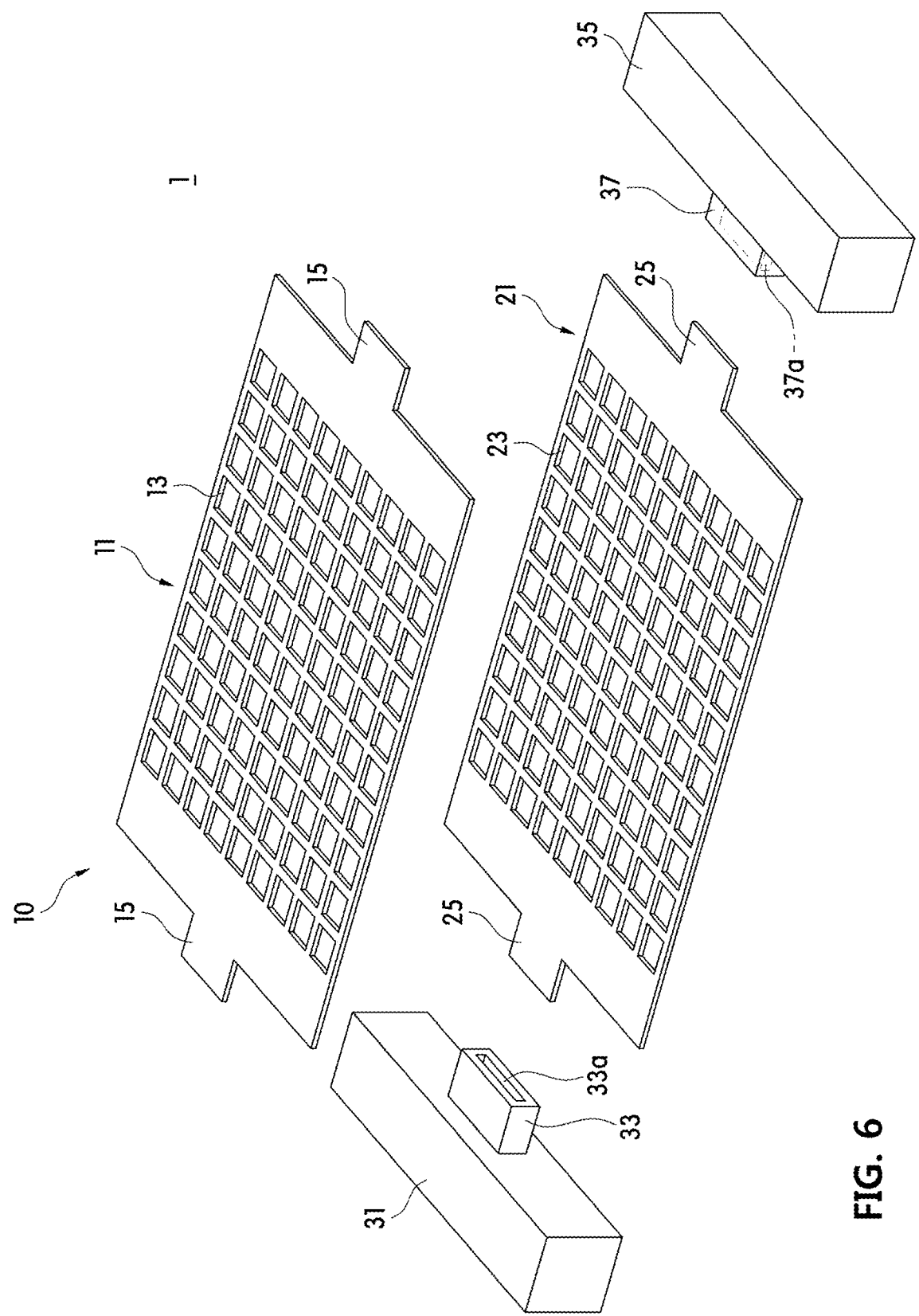
FIG. 6 an exploded perspective view illustrating a structure according to an embodiment of the present invention.

Specifically, the support 10 includes at least two platy structures 11, 21 as shown in FIG. 6, and the two platy structures 11, 21 are laminated. Also, the first material 60 may be disposed between the two platy structures 11, 21.

Here, the platy structure may have a rectangular cross section, but the present invention is not limited thereto. Also, each of openings 13, 23 which allow a reactant to access the inside from the outside may be formed in each of the at least two platy structures.

In addition, the platy structures 11, 21 are arranged to be parallel to each other, one on top of the other, and each may be a sheet-type structure in the form of a lattice.

Meanwhile, although in the description provided above, the platy structures 11, 21 are two separate entities arranged to be parallel to each other, the present invention is not limited thereto. The platy structures 11, 21 may be formed as one support 10.

In addition, it should be understood that, in the support 10, a plurality of platy structures 11, 21 may be laminated while being arranged to be parallel to each other, one on top of the other. Also, the support 10 may have a cross-section in the shape of a polygon such as a rectangle, a rhombus, a hexagon, or the like, or a circle or an ellipse, but the present invention is not limited thereto.

Meanwhile, in an embodiment of the present invention, the support 10 includes protrusions 15, 25 formed at both ends thereof, and thus may be coupled with the density-adjusting body 30. In an embodiment of the present invention, the protrusions 15, 25 of the support 10 are press-fitted into coupling grooves 33a, 37a of the density-adjusting body 30, and thus coupled with the density-adjusting body 30, but the present invention is not limited thereto.

The density-adjusting body 30 includes a first floating body 31 and a second floating body 35 as a pair. Also, each of the first and second floating bodies 31, 35 may be coupled to either end of the support 10, and the density-adjusting body 30 which has a rectangular parallelepiped shape may include a void S formed so that air may be filled therein.

Therefore, the structure 1 according to an embodiment of the present invention may float on a liquid.

In this case, a suspension degree of the density-adjusting body 30 may be adjusted in accordance with not only the volume of the void but also a material of the density-adjusting body 30 and a composition of the material as in the structure 1' according to the first embodiment.

In an embodiment of the present invention, the density-adjusting body 30 may be formed in any shape and of any material as long as it floats on a liquid.

Figure 5:
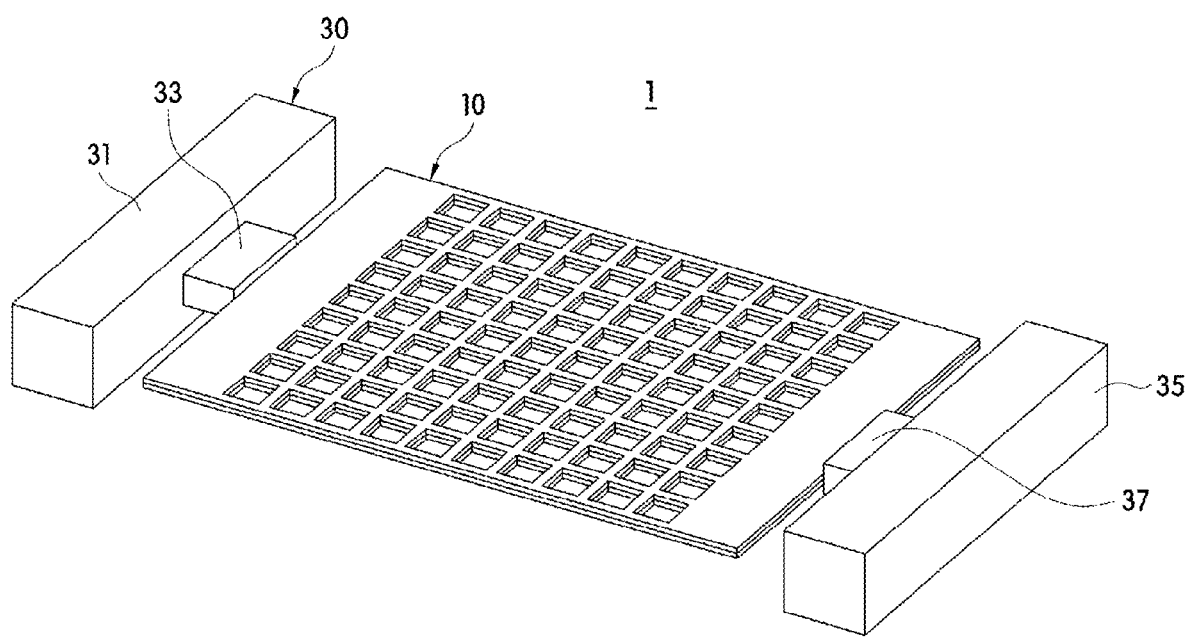
FIG. 5 is a perspective view illustrating a second embodiment of a structure according to an embodiment of the present invention.

Referring to FIG. 5, in an embodiment of the present invention, each of the density-adjusting bodies 30 may include protruded portions 33, 37 formed in a rectangular parallelepiped shape.

In addition, the protruded portions 33, 37 may include the coupling grooves 33a, 37a into which the protrusions 15, 25 of the support 10 are press-fitted. In this case, the coupling grooves 33a, 37a may be formed complementary to the protrusions 15, 25 so that the coupling grooves are press-fitted into the protrusions.

The carrier 50 is disposed between the two platy structures 11, 21 as shown in FIG. 7, and may allow the first material 60 to be immobilized between the platy structures 11, 21.

In this case, the first material 60 may be immobilized to a surface of the carrier 50 by being combined with the same. In an embodiment of the present invention, the carrier 50 may be a nanostructure, but the present invention is not limited thereto.

Here, the first material 60 may be any one selected from an organic catalyst, an inorganic catalyst, and a biomolecule.

In an embodiment of the present invention, in order to combine the first material 60 with the support 10, the support is formed as a nanostructure, and thus the first material may be directly combined with the support.

Briefly describing a method of preparing the structure 1, first, the carrier 50 combined with an enzyme is combined with an upper surface of the platy structure 21 disposed at a lower part of the support 10, the other platy structure 11 is laminated on the platy structure 21, and then the first material 60 is combined with the carrier 50 between the pair of platy structures.

In addition, the protrusions 15, 25 of the support 10 are press-fitted to the coupling grooves 33a, 37a formed at the first floating body 31 and the second floating body 35, which are fabricated using a 3D printer, respectively, and thus the structure 1 may be prepared.

Meanwhile, referring to FIGS. 5 to 7, it is shown and described that each density-adjusting body is coupled to either end of one support, but the present invention is not limited thereto. For example, a plurality of supports may be coupled to one density-adjusting body.

In the structure 1' according to the first embodiment and the structure 1 according to the second embodiment, the first material may be directly combined with the support 10 and the body 10'. In this case, when the first material is directly combined with the support 10 and the body 10', one of adsorption, covalent bonding and ionic bonding using a functional group, and an adhesive material based on a catechol group such as polydopamine or polynorepinephrine may be used.

In addition, the first material may be combined with the carrier 50 to be combined with the support 10 and the body 10'.

In this case, the carrier may be combined with surfaces of the support 10 and the body 10' by using one of adsorption, covalent bonding and ionic bonding using a functional group, and an adhesive material based on a catechol group such as polydopamine or polynorepinephrine.

In an embodiment of the present invention, the carrier 50 includes a functional group, which reacts with the first material 60, and thus the first material may be combined with the carrier. In this case, a functional group to be reacted varies in accordance with the first material 60, and thus a specific functional group may be used in accordance with the first material.

In addition, in an embodiment of the present invention, the first material 60 may be combined with the carrier 50 through simple adsorption without the involvement of a functional group.

In an embodiment of the present invention, the carrier 50 may be a polymer fiber including a functional group. In this case, the carrier 50 may be a polymer fiber aggregate formed of a plurality of polymer fibers.

The carrier 50 may be the polymer fibers in a part of the polymer fiber aggregate, and the carrier 50 may form a column of polymer fibers protruding toward an outer surface of the body in a vertical direction. In this case, the column may be formed in various shapes such as a straight line, a streamline, an S shape, and the like, and preferably, the majority of the column is formed in a direction perpendicular to the longitudinal direction of a medium.

In an embodiment of the present invention, the first material 60 such as an organic catalyst, an inorganic catalyst, and a biomolecule may be directly or indirectly combined with a functional group of the carrier 50.

Specifically, in an embodiment of the present invention, an organic catalyst, an inorganic catalyst, and a biomolecule may be directly combined with a functional group through covalent bonding and ionic bonding. Preferably, an organic catalyst, an inorganic catalyst, and a biomolecule are combined with a functional group through covalent bonding.

In an embodiment of the present invention, the support 10 and the density-adjusting body 30 in the structure 1 according to the second embodiment and the body 10' in the structure 1' according to the first embodiment may include one or more materials selected from the group consisting of an acrylonitrile butadiene styrene (ABS) resin, polycarbonate (PC), polyvinyl alcohol (PVA), polystyrene (PS), polylactic acid, polycaprolactam, polycaprolactone, poly(lactic-co-glycolic acid), polyacrylonitrile, polyester, polyethylene, polyethyleneimine, polypropylene oxide, polyurethane, polyglycolic acid, polyethylene terephthalate, poly(methyl methacrylate), polydimethylsiloxane, Teflon, a filter paper, glass, a gold-plated substrate, and silicon.

In addition, in an embodiment of the present invention, the carrier may include at least one selected from polymer fibers, electroconductive polymers, porous particles, spherical particles, nanoparticles, beads, carbon nanotubes, wires, pillars, graphene, fullerenes, and polydopamine.

Additionally, the polymer fiber may include a functional group.

In addition, the polymer fiber including a functional group may be a polymer fiber including a functional group formed by modifying a polymer fiber including one or more selected from polyaniline, polypyrrole, polythiophene, acrylonitrile butadiene styrene, polylactic acid, polyvinyl alcohol, polyacrylonitrile, polyester, polyethylene, polyethyleneimine, polypropylene oxide, polyvinylidene fluoride, polyurethane, polyvinyl chloride, polystyrene, polycaprolactam, poly(lactic-co-glycolic acid), polyglycolic acid, polycaprolactone, polyethylene terephthalate, poly(methyl methacrylate), polydimethylsiloxane, Teflon, collagen, poly(styrene-co-maleic anhydride), nylon, cellulose, chitosan, and silicon.

In this case, the polymer fiber including a functional group according to an embodiment of the present invention may be a copolymer of a first monomer including one or more selected from aniline, pyrrole, lactic acid, vinyl alcohol, acrylonitrile, ethylene, ethyleneimine, propylene oxide, urethane, vinyl chloride, styrene, caprolactam, caprolactone, ethylene terephthalate, methyl methacrylate, dimethylsiloxane, Teflon, collagen, nylon, cellulose, chitosan, and silicon and a second monomer including one or more selected from 1-aminobenzoic acid, 2-aminobenzoic acid, 3-aminobenzoic acid, 1-phenylenediamine, 2-phenylenediamine, 3-phenylenediamine, pyrrole-1-carbaldehyde, pyrrole-2-carbaldehyde, and pyrrole-3-carbaldehyde.

In addition, the first material may include at least one selected from an organic catalyst, an inorganic catalyst, a biomolecule, and a microorganism.

The organic catalyst may include one or more selected from the group consisting of carbonic anhydrases, glucose oxidases, trypsin, chymotrypsin, subtilisin, papain, thermolysin, lipases, peroxidases, acylases, lactonase, proteases, tyrosinase, laccases, cellulases, xylanases, organophosphohydrolase, cholinesterases, formate dehydrogenases, aldehyde dehydrogenases, alcohol dehydrogenases, glucose dehydrogenases, and glucose isomerase.

The inorganic catalyst may include one or more selected from the group consisting of platinum, rhodium, palladium, lead, iridium, rubidium, iron, nickel, zinc, cobalt, copper, manganese, titanium, ruthenium, silver, molybdenum, tungsten, aluminum, antimony, tin, bismuth, barium, osmium, nitrogen oxide, copper oxide, manganese oxide, titanium oxide, vanadium oxide, and zinc oxide.

The biomolecule may include one or more selected from the group consisting of albumin, insulin, collagen, an antibody, an antigen, protein A, protein G, avidin, streptavidin, biotin, a nucleic acid, a peptide, a lectin, and a carbohydrate.

The microorganism may include one or more selected from the group consisting of *Bacillus subtilis*, *Bacillus licheniformis*, *Bacillus polyfermenticus*, *Bacillus mesentericus*, *Saccharomyces cerevisiae*, *Clostridium butyricum*, *Streptococcus faecalis*, *Streptococcus faecium*, *Micrococcus caseolyticus*, *Staphylococcus aureus*, *Lactobacillus casei*, *Lactobacillus plantarum*, *Leuconostoc mesenteroides*, *Debaryomyces nicotianae*, *Acinetobacter calcoaceticus*, *Alcaligenes odorans*, *Aromatoleum aromaticum*, *Geobacter metallireducens*, *Dechloromonas aromatic*, *Arthrobacter* sp., and *Alcanivorax borkumensis*. Meanwhile, a method of adjusting buoyancy through adjustment of a gas or a liquid stored in the void will be described in detail below.

Specifically, referring to FIGS. 8 to 11, the structures 1, 1' according to an embodiment of the present invention may move in a vertical direction at an interface between two materials so that the structures are suspended at an interface between two liquids, that is, a first liquid 3 and a second liquid 5, or between a gas and a liquid.

Since the amounts of a gas and the liquids 3, 5 present in the void S affect buoyancy, buoyancy is adjusted by adjusting the amounts thereof.

The void S may be made of a material in which deformation such as an increase or a decrease in a volume caused by the pressure exerted by the floating bodies 31, 35 and the body 10' does not occur because it is a space for storing a gas and the liquids 3, 5.

In an embodiment of the present invention, when the volumes of the floating bodies 31, 35 and the body 10' are changed, it may be difficult to adjust buoyancy because a change in buoyancy caused by the change in the volumes needs to be taken into account.

Figure 9:
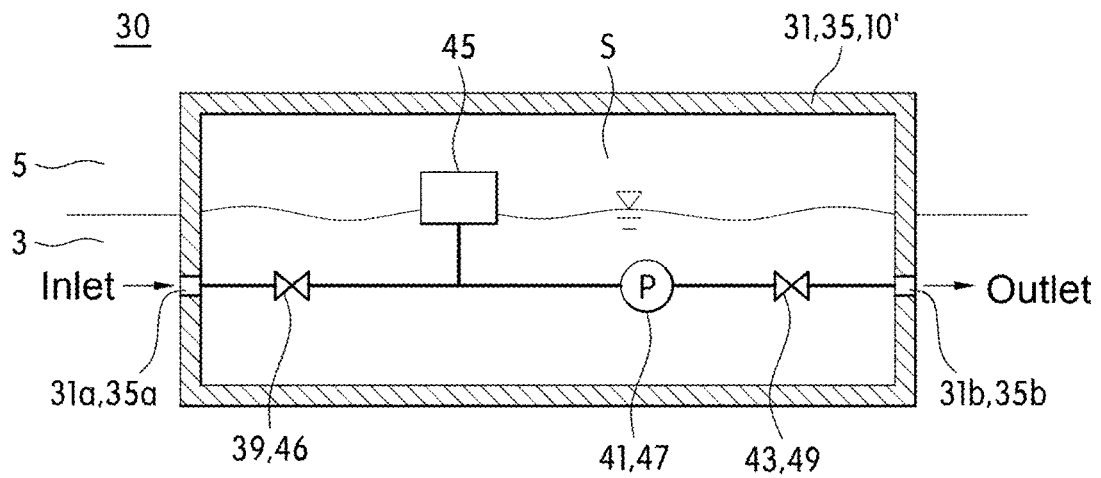

Referring to FIG. 9, the void S may include a first valve 39, a first pump 41, a second valve 43, and an air tank 45.

In this case, inlets 31a, 35a configured to introduce a fluid and outlets 31b, 35b configured to discharge a fluid are formed in the side surfaces of the body 10' according to the first embodiment and the floating bodies 31, 35 according to the second embodiment as shown in FIG. 9.

In an embodiment of the present invention, the body 10' according to the first embodiment and the floating bodies 31, 35 according to the second embodiment adjust the amount of a fluid (air or the liquids 3, 5) present in the void S through the inlets 31a, 35a and the outlets 31b, 35b.

Meanwhile, the first valve 39 and a third valve 46 are installed in the void S, and one end thereof is connected to each of the inlets 31a, 35a. Therefore, the first valve 39 and the third valve 46 serve to open or close a flow path through which a fluid is introduced into the void.

Therefore, when the first valve 39 is open, the first liquid 3 and the second liquid 5 are introduced from the outside of the body 10' according to the first embodiment and the floating bodies 31, 35 according to the second embodiment to the inside thereof. Accordingly, buoyancy is decreased, and thus the structures 1, 1' according to an embodiment of the present invention may be moved downward.

In addition, the second valve 43 and a fourth valve 49 are installed in the body 10' according to the first embodiment and the floating bodies 31, 35 according to the second embodiment, and one end thereof is connected to each of the outlets 31b, 35b. Therefore, the second valve 43 and the fourth valve 49 serve to open or close a flow path through which a fluid is discharged to the outside of the body 10' according to the first embodiment and the floating bodies 31, 35 according to the second embodiment.

Additionally, the other end of the second valve 43 and the fourth valve 49 is connected to the body 10' according to the first embodiment and the floating bodies 31, 35 according to the second embodiment, and thus the second valve 43 and the fourth valve 49 allow the first liquid 3 and the second liquid 5, which are fluids in the void, to move to the outside through a transferring operation of the pump.

In addition, when the first pump 41 performs the operation of transferring fluids, the first liquid 3 and the second liquid 5, which are fluids in the void, are discharged to the outside through the second valve 43. As a result, the amount of fluids in the void is decreased, and thus the buoyancy of the body 10' according to the first embodiment and the floating bodies 31, 35 according to the second embodiment is increased.

In this case, the first pump 41 is a pump configured to discharge a fluid by allowing a flow of the fluid in one direction, but the present invention is not limited thereto. Alternatively, the first pump 41 may be a pump configured to allow the flow of fluid in both directions. When the first pump 41 is a bidirectional pump, a fluid may be introduced through the first valve 39 by operating the first pump.

In addition, the air tank 45 fills the void S with as much air as the discharge amount of the first liquid 3 and the second liquid 5, which are fluids, after the fluids are discharged through the first pump 41, and thus the buoyancy of the body 10' according to the first embodiment and the floating bodies 31, 35 according to the second embodiment is increased.

In this case, the air tank 45 may be an air cylinder tank, and the inside thereof may be filled with compressed air. Also, the air tank 45 is effective in adjusting buoyancy when the void S is in a position where air cannot be obtained from the atmosphere.

Figure 10:
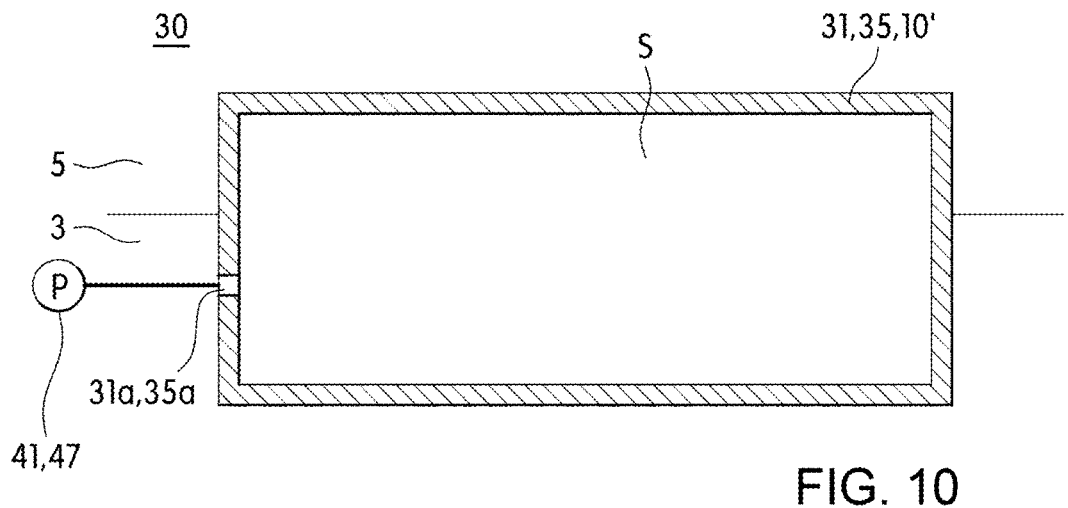

Referring to FIG. 10, in an embodiment of the present invention, there may be a fluid in the void, and the first pump 41 may be installed outside the body 10' according to the first embodiment and the floating bodies 31, 35 according to the second embodiment, and thus connected to one end of the body 10' according to the first embodiment and the floating bodies 31, 35 according to the second embodiment.

In this case, the first pump 41 may be a unidirectional or bidirectional pump, and allow a fluid (air or the liquids 3, 5) to be introduced into the void S or discharged to the outside to adjust buoyancy.

Figure 11:
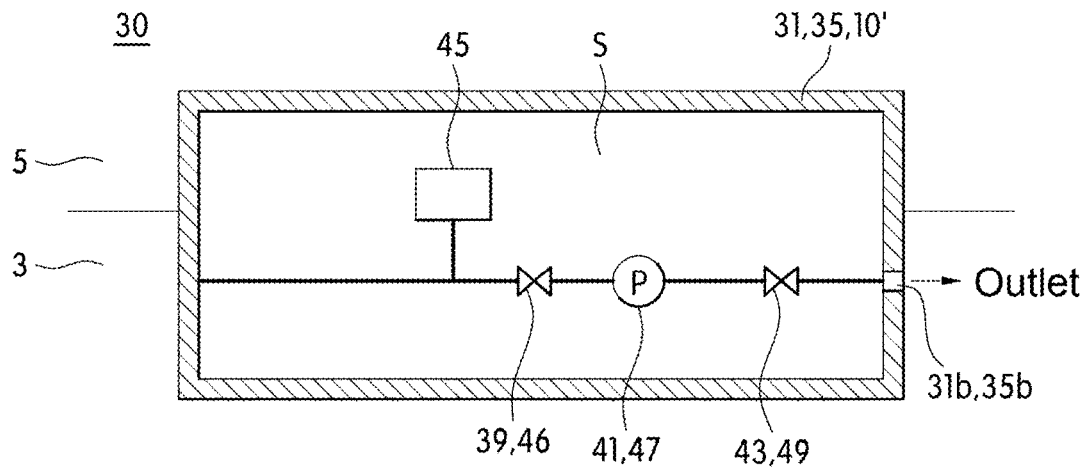

Referring to FIG. 11, the void S may include a first valve 39, a first pump 41, a second valve 43, and an air tank 45. In this case, outlets 31b, 35b configured to discharge a fluid are formed in the side surfaces of the body 10' according to the first embodiment and the floating bodies 31, 35 according to the second embodiment as shown in FIG. 11.

Meanwhile, the first valve 39 and a third valve 46 are installed in the void, and one end thereof is connected to the air tank 45. Therefore, the first valve 39 and the third valve 46 serve to open or close a flow path through which a fluid is introduced into the void.

In an embodiment of the present invention, when the first valve 39 is open, compressed air in the air tank 45 of the void is introduced into the void S. Accordingly, buoyancy is decreased, and thus the structures 1, 1' according to an embodiment of the present invention may be moved downward.

In addition, the other end of the second valve 43 is connected to the first pump 41, and thus the second valve 43 allows air as a fluid in the void to move to the outside through a transferring operation of the pump.

Referring to FIG. 11, when the first pump 41 performs the operation of transferring fluids, air as a fluid in the void may be discharged to the outside through the second valve 43.

Accordingly, the amount of air in the void is decreased, and thus the buoyancy of the body 10' according to the first embodiment and the floating bodies 31, 35 according to the second embodiment is increased. As a result, the structures 1, 1' according to an embodiment of the present invention may be moved upward.

Meanwhile, referring to FIGS. 8 to 11, it is shown and described that the structures 1, 1' are suspended at an interface between a liquid and a liquid, but the structures 1, 1' may also be suspended at an interface between a gas and a liquid. Descriptions of the structures 1, 1' which are suspended at an interface between a gas and a liquid are the same as that described above.

The structures 1, 1' having components as described above may react at an interface between a gas and a liquid or between a liquid and a liquid.

First, a reaction at an interface between a gas and a liquid will be described with reference to FIGS. 12A and 12B.

For example, a liquid on which the structures 1, 1' float may be sea water containing microalgae. In this case, when a reactant is $CO_2$ in the atmosphere, a first material may be an enzyme.

Figure 12A:
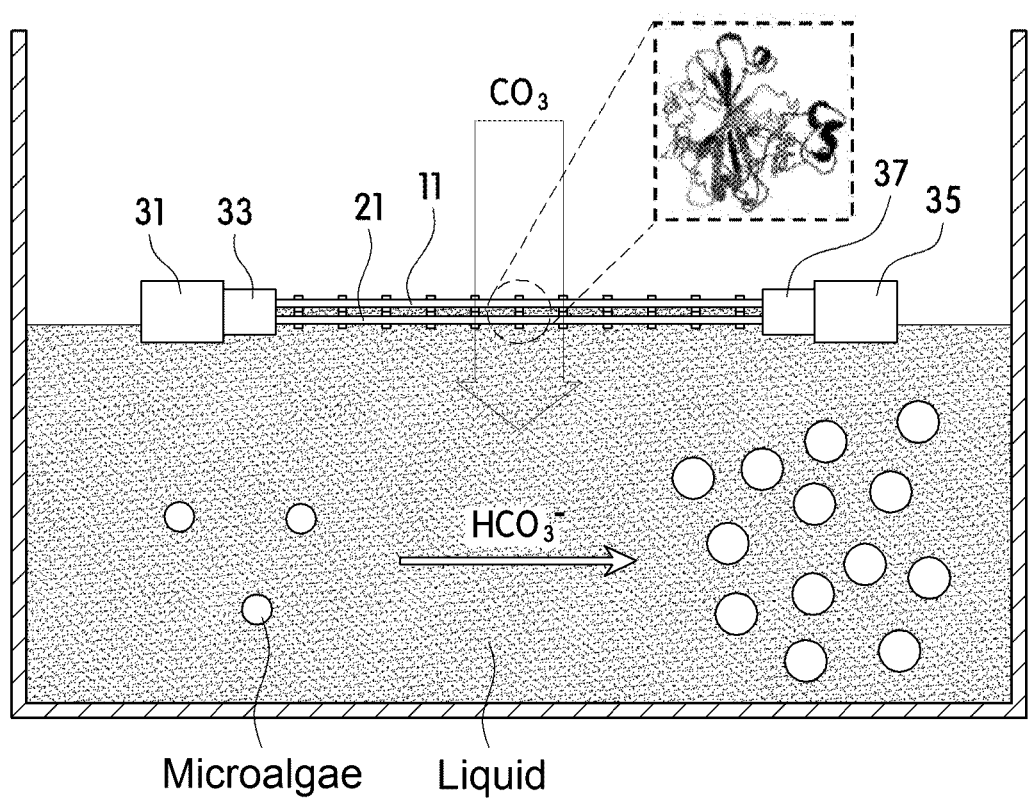
FIGS. 12A and 12B illustrate a case in which a structure according to an embodiment of the present invention is used at an interface between a gas and a liquid.

Referring to FIG. 12A, $CO_2$ in the atmosphere as a reactant may react with the first material 60 supported in the bodies 10, 10' of the structures 1, 1' to form $HCO_3^-$. Also, microalgae contained in sea water may grow due to $HCO_3^-$.

Therefore, the structures 1, 1' according to an embodiment of the present invention may collect $CO_2$ due to the first material, and the growth of microalgae contained in sea water may be promoted due to the collected $CO_2$.

As another example, a liquid on which the structures 1, 1' float may include oil. In this case, when a reactant is oil, the first material 60 may be an oil-decomposing microorganism.

Figure 12B:
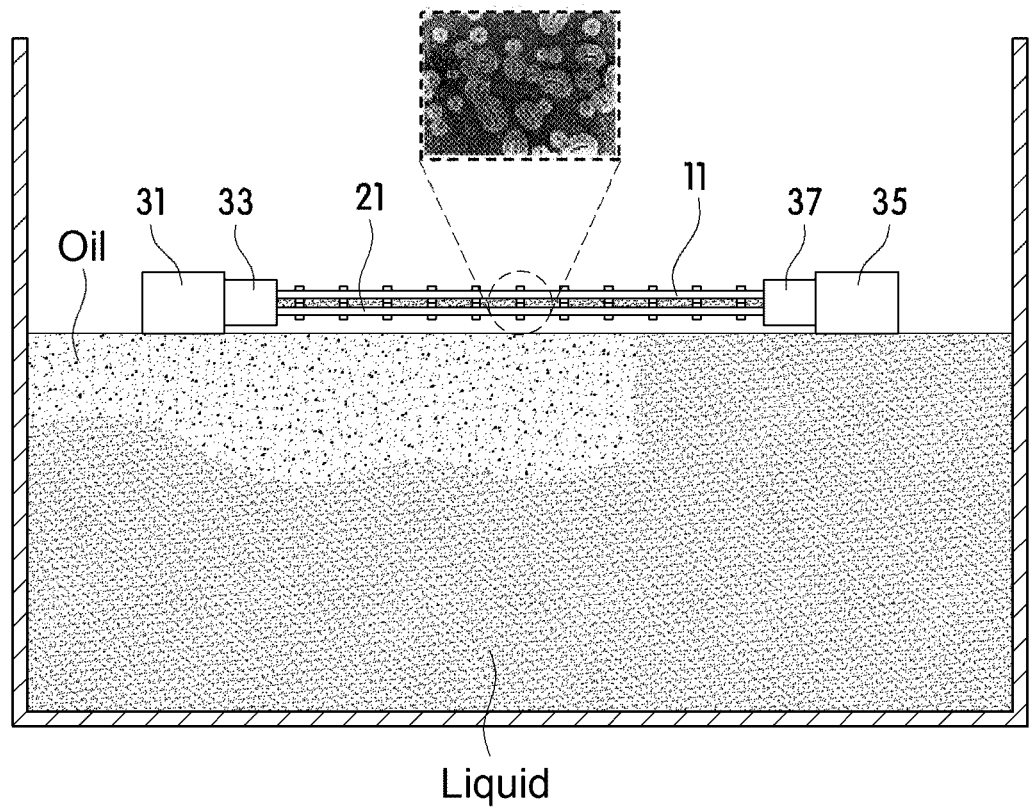

Referring to FIG. 12B, oil as a reactant reacts with an oil-decomposing microorganism which is the first material 60 supported in the bodies 10, 10' of the structures 1, 1' and thus may be removed. As a result, oil in a liquid may be removed to purify the liquid.

The structure according to an embodiment of the present invention may include a microorganism as a pollution source or a signaling molecule which promotes expression of a microorganism and formation of a biofilm, and the first material may be an enzyme for antifouling.

For example, the first material may be a carbonic anhydrase, and a polymer nanofiber as the carrier 50, a cross-linking agent, and a settling agent may be used to immobilize the first material to the carrier.

Figure 13:
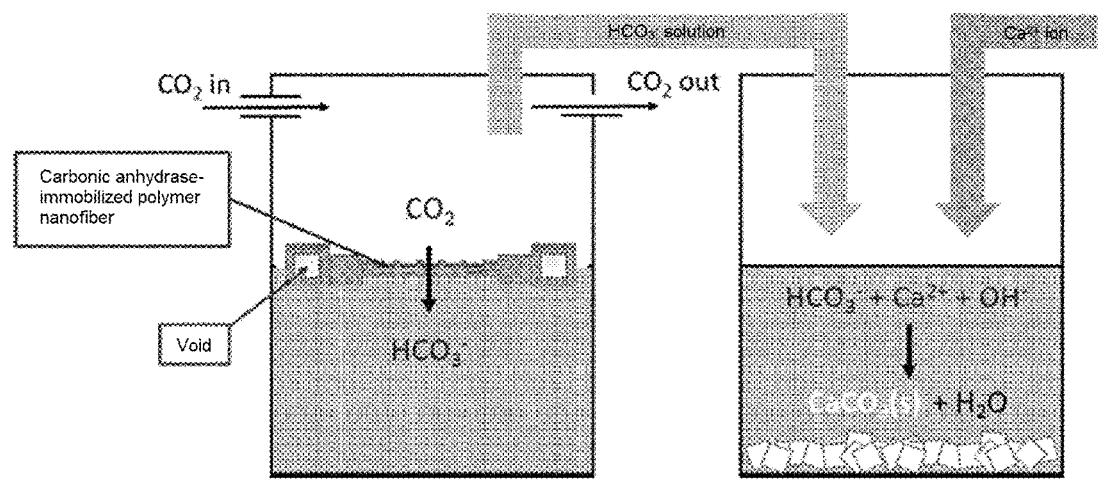
FIG. 13 is a schematic diagram illustrating a process of collecting carbon dioxide and converting carbon dioxide to calcium carbonate by a first material by using a structure according to an embodiment of the present invention.

Referring to FIG. 13, in an embodiment of the present invention, polystyrene (PS; MW=950,400) and poly(styrene-co-maleic anhydride) (PSMA; MW=224,000) may be used as a polymer for preparing the polymer nanofiber used as the carrier 50, and tetrahydrofuran (THF) and acetone may be used as the organic solvents for dissolving the polymer. The polymer nanofiber may be prepared using an electrospinning method.

Referring to FIG. 13, in an embodiment of the present invention, covalent bonding between an amine group in a carbonic anhydrase as a first material and maleic anhydride which is a first functional group in a polymer nanofiber as the carrier 50 is induced, and glutaraldehyde as a cross-linking agent and ammonium sulfate as a settling agent are used to additionally induce cross-linking between first materials.

Referring to FIG. 13, a combined material of the first material and the carrier is included between the support 10 of the structure 1.

Referring to FIG. 13, the structure 1 was positioned at an interface between carbon dioxide gas and a Tris-HCl (pH 8.0) solution, and then an experiment in which carbon dioxide in a gaseous state is converted into calcium carbonate through a carbonic anhydrase was performed.

Figure 14:
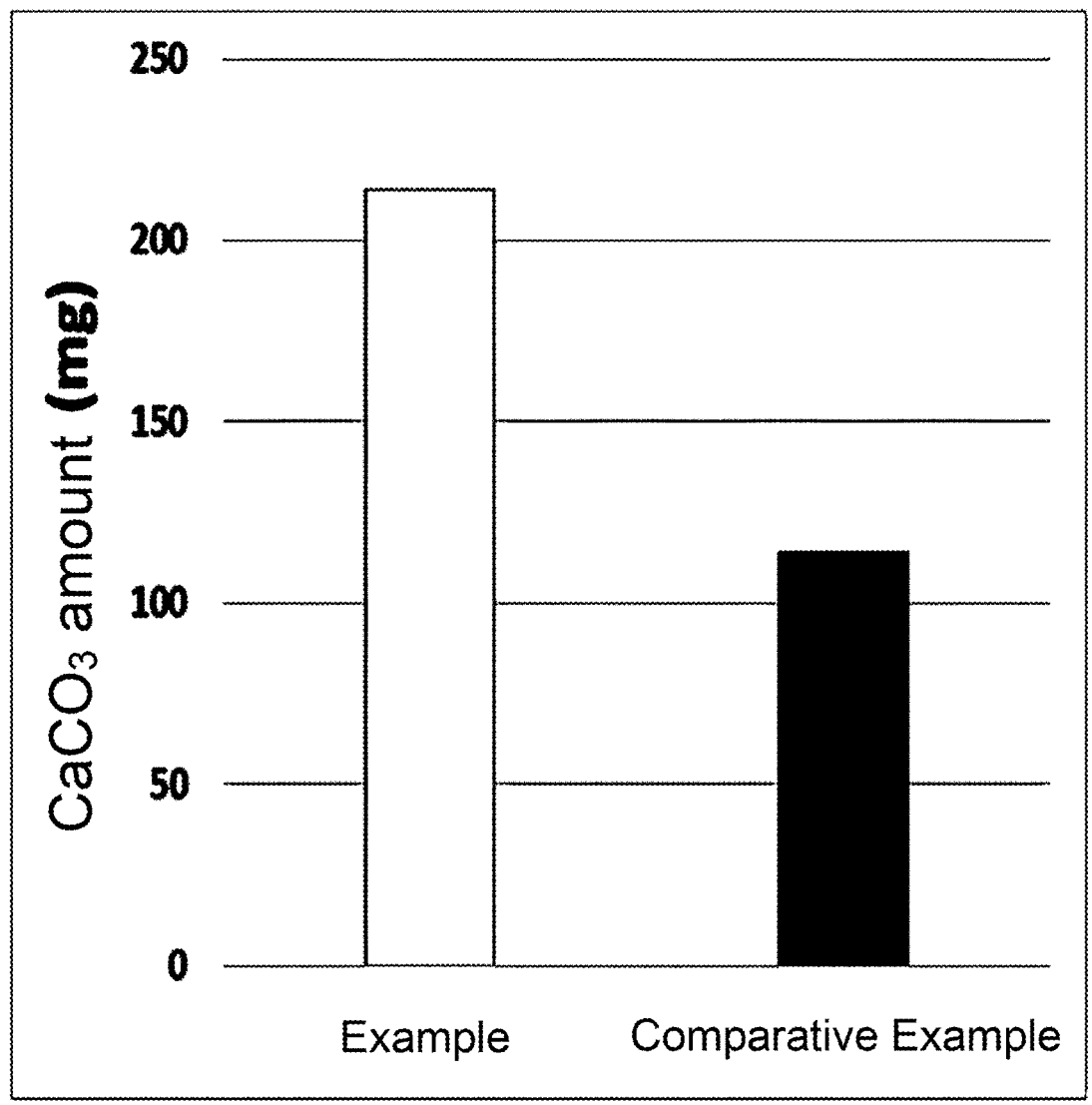
FIG. 14 is a result of an experimental example in which the process of collecting carbon dioxide and converting carbon dioxide to calcium carbonate in FIG. 13 is applied using a structure according to an embodiment of the present invention.

Referring to FIG. 14, Example is a case in which the carrier 50 includes a first material, and Comparative Example is a case in which the carrier 50 does not include a first material. As a result of comparing Example and Comparative Example, it can be confirmed that 214 and 114 mg of calcium carbonate are produced, respectively, during a reaction time of 20 minutes.

Therefore, the structure 1' according to an embodiment of the present invention may produce 1.9-fold more calcium carbonate through the support including a first material.

The structure according to an embodiment of the present invention may be positioned at an interface between a gas and a liquid, and may include the first material for easily combining with or converting a material present in a gas or liquid.

Next, a process of converting a reactant at an interface between a liquid and a liquid using the structure will be described.

For example, a process of converting a reactant at an interface between a liquid and a liquid according to an embodiment of the present invention may use a reaction container 7 and the structure 1 or 1'.

The reaction container 7 may accommodate a first liquid 3 and a second liquid 5. In this case, the two liquids may be the first liquid 3 and the second liquid 5 which are not interacting with each other, wherein the second liquid may be positioned on the first liquid, or the first liquid may be positioned on the second liquid, but the present invention is not limited thereto.

The structures 1, 1' may support the first material 60 and may be suspended at an interface between the first liquid 3 and the second liquid 5. In this case, the first material 60 may be formed to react with a reactant (not shown) present in any one of the first liquid 3 and the second liquid 5.

A liquid on which the structures 1, 1' float may be water including an organic acid (reactant).

Here, the organic acid in water as a reactant may react with the first material 60 supported in the support 10 of the structure 1 and the body 10' of the structure 1' to form an ester.

In addition, the structures 1, 1' may allow any material present in the first liquid to be removed by the first material 60 or a reactant to be converted into a product suitable for use.

As such, each liquid in the process of converting a reactant at an interface between a liquid and a liquid may include a reactant (or solute) and a solution, or any one of the liquids may include only a solution.

In addition, the liquids (i.e., solutions) may be the reactants themselves. In this case, since each liquid is a reactant, a new product may be produced or the reactant may be decomposed at an interface between the liquids by a corresponding reaction caused by the reactants.

Additionally, the first liquid and the second liquid may be immiscible with each other, and the densities of the first liquid, the second liquid, the structure may satisfy Equation 1 below.

$$\text{Density of first liquid} < \text{Density of structure} < \text{Density of second liquid} \quad \text{[Equation 1]}$$

Figure 15:
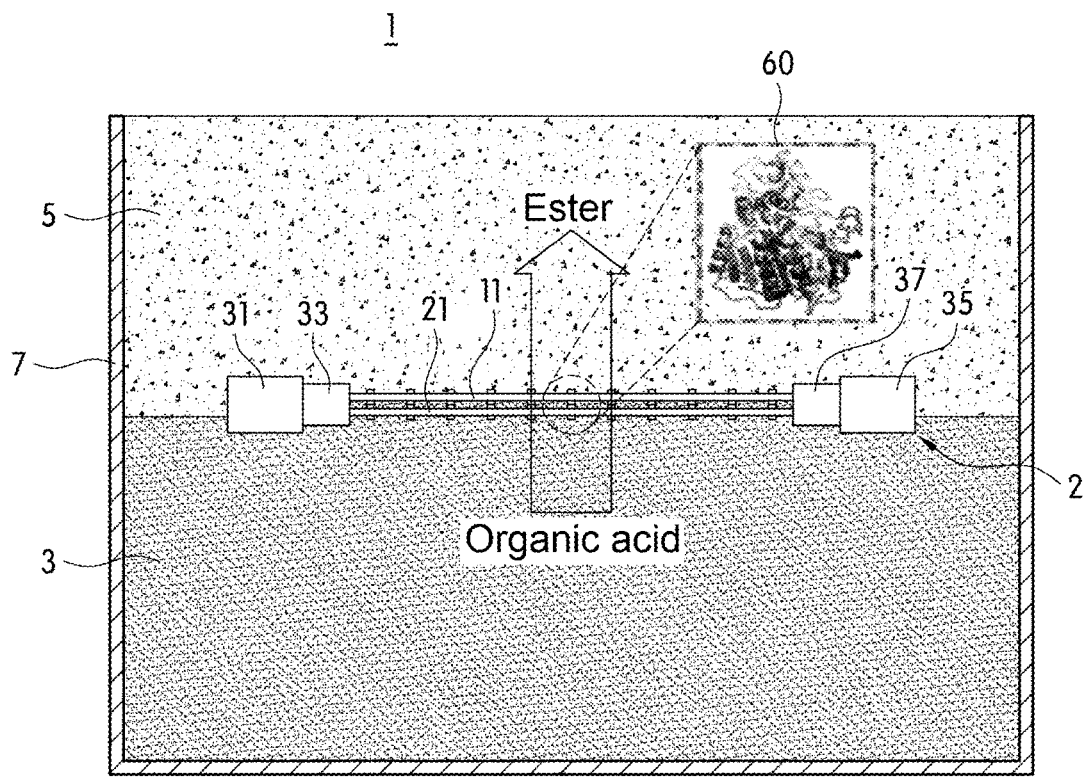
FIG. 15 is a schematic diagram illustrating a process of converting a reactant at an interface between a liquid and a liquid using a structure according to an embodiment of the present invention.

Referring to FIG. 15, the structures 1, 1' are present at an interface formed between the first liquid 3 and the second liquid 5 (that is, the structures are suspended in the first liquid), and a reactant in the first liquid and/or a reactant in the second liquid may form a product due to a first material in the structure. Also, the product thus formed is present in the first liquid and/or the second liquid, preferably in the second liquid.

In the present invention, the structure may include a first material which catalyzes a reaction of the reactant. The reactant may be included in one or more liquids selected from the first liquid and the second liquid.

In addition, the first liquid and the second liquid may be the reactants themselves. In this case, since each of the first liquid and the second liquid is a reactant, a new product may be produced or the reactant may be decomposed at an interface between the first liquid and the second liquid by a corresponding reaction caused by the reactants. Also, a first component and a second component included in the first liquid and the second liquid, respectively, may be the reactants. In this case, the first component and the second component may react at an interface between the liquids.

The first liquid and the second liquid each independently may include one or more selected from water, isooctane, dichlorohexane, hexane, heptane, cyclohexane, diethylether, octane, ethyl acetate, dichloromethane, chloroform, carbon tetrachloride, toluene, tetrahydrofuran, acetone, pyridine, ethylene glycol, and butanediol, particularly, one or more selected from the group consisting of water, isooctane, 1,6-dichlorohexane, hexane, and heptane, and more particularly, water and isooctane.

In a specific example of the conversion of a reactant, when it is assumed that a first liquid is water, a second liquid is isooctane, and an alcohol and an organic acid which are reactants are included in the first liquid, the reactants included in the first liquid may react due to a lipase (first material) to form an ester compound. When the ester compound as a product is continuously present in the first liquid, the ester compound reversely reacts due to a reversible reaction of a catalyst to form an organic acid and an alcohol which are reactants, and thus the yield of a desired product may be significantly reduced. Accordingly, it is preferable that a product produced by the reaction of a reactant occurring in the first liquid is separated from the first liquid as soon as possible. When a second liquid having a solubility higher than that of a first liquid with respect to a product is used, the product may move from the first liquid to the second liquid and may be stored while being dissolved in the first liquid and/or the second liquid, preferably, the second liquid.

In addition, the product in the first liquid needs to move quickly to the second liquid before the reaction is reversed to favor the reactants. When a product is produced in the first liquid of an interface between the first liquid as a reaction site and the second liquid as a transfer and storage site, the product may be transferred as quickly as possible to the second liquid. Therefore, when a first material is present at an interface between two liquids, a product is transferred to and stored in a second liquid, and thus the yield of a desired product may be significantly increased.

Therefore, in the present invention, a reaction is performed by applying a first material into a structure which may be suspended at an interface between a first liquid and a second liquid, and thus a reaction yield may be improved.

Figure 16:
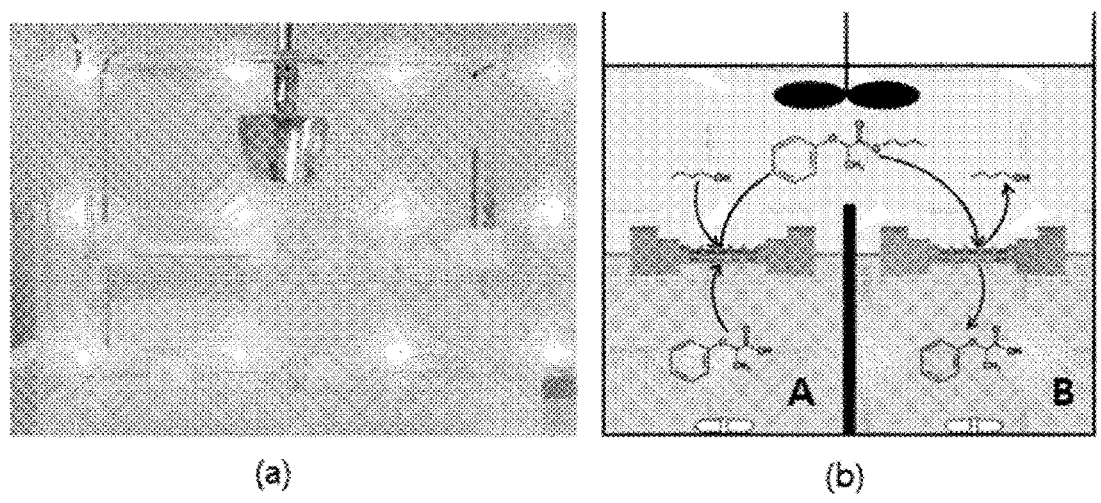
FIG. 16, in panels (a) and (b), shows an image and a concept diagram illustrating a reaction process of a structure according to Example 5 of the present invention.

In addition, in the present invention, as shown in FIG. 16, panels (a) and (b), a specific material in a specific liquid is transferred to and stored in another liquid separated from the specific liquid and, and thus the specific material in the specific liquid may be selectively separated or obtained at high concentration.

A detailed description thereof will be provided as follows. According to the process of converting a reactant of the present invention, there are a first liquid, a second liquid, and a third liquid, the second liquid comes in contact with the first liquid and the third liquid to form interfaces, and the first liquid and the third liquid are separated from each other. Also, the structure includes a first structure and a second structure, the first structure may be present at an interface between the first liquid and the second liquid, and the second structure may be present at an interface between the second liquid and the third liquid.

In this case, the first liquid, the second liquid, the third liquid, the first structure, and the second structure may satisfy Equation 2 and Equation 3 below.

Density of first liquid <Density of first structure
<Density of second liquid  [Equation 2]

Density of second liquid <Density of second structure <Density of third liquid  [Equation 3]

The first liquid, the second liquid, the third liquid each independently may include one or more solvents selected from the group consisting of water, isooctane, dichlorohexane, hexane, heptane, cyclohexane, diethylether, octane, ethyl acetate, dichloromethane, chloroform, carbon tetrachloride, toluene, tetrahydrofuran, acetone, pyridine, ethylene glycol, and butanediol.

In addition, the first structure and the second structure each may include the same first material or different first materials.

As shown in FIG. 16, panel (b), a reactant in the first liquid and a reactant in the second liquid form an intermediate by the first material in the first structure, the intermediate is present in the first liquid and/or the second liquid, preferably, at higher concentration in the second liquid than in the first liquid, and the intermediate forms a final product by the first material in the second structure. That is, as the process of converting a reactant proceeds, the concentration of a reactant in the first liquid decreases, and the concentration of a final product in the third liquid increases. From this result, a specific material may be separated from the first liquid (A in FIG. 16, panel (b)) by being transferred to the second liquid (B in FIG. 16, panel (b)), and may be obtained at high concentration.

In addition, a reactant in the first liquid and a final product in the third liquid may be the same material or different materials as described above, and may vary depending on the type of reactant in the second liquid and the type of first material in the second structure.

A detailed description thereof will be provided with reference to FIG. 16, panel (b) as follows. The first liquid is a liquid in which 2-phenoxypropionic acid is dissolved in a water solvent, the third liquid includes only water, and the second liquid is a liquid in which butyl alcohol is dissolved in an isooctane solvent. Also, the first liquid and the third liquid are separated by a barrier, and the second liquid comes in contact with each of the first liquid and the third liquid to form interfaces.

In addition, when a reaction is initiated after the first structure and the second structure are positioned in such a way that the first structure including a first material is suspended at an interface between the first liquid and the second liquid and the second structure including a first material is suspended at an interface between the second liquid and the third liquid, 2-phenoxypropionic acid in the first liquid and butyl alcohol in the second liquid are reacted to form butyl-2-phenoxypropanoate as a product, which is present in the second liquid. In this case, a reaction rate is increased due to a first material in the first structure, and the yield of butyl-2-phenoxypropanoate is increased. Also, butyl-2-phenoxypropanoate in the second liquid reacts with a first material in the second structure present at an interface between the second liquid and the third liquid to form butyl alcohol and 2-phenoxypropionic acid, and 2-phenoxypropionic acid is dissolved in the second liquid. That is, as the reactions proceed, 2-phenoxypropionic acid, which had been present in the first liquid but not in the second liquid before the reactions were initiated, transfers from the first liquid to the second liquid, and thus 2-phenoxypropionic acid can be separated from the first liquid and obtained at high concentration.

Through this method, when various materials are present in a liquid, a specific material may be separated from the liquid and obtained at high concentration.

Figure 17:
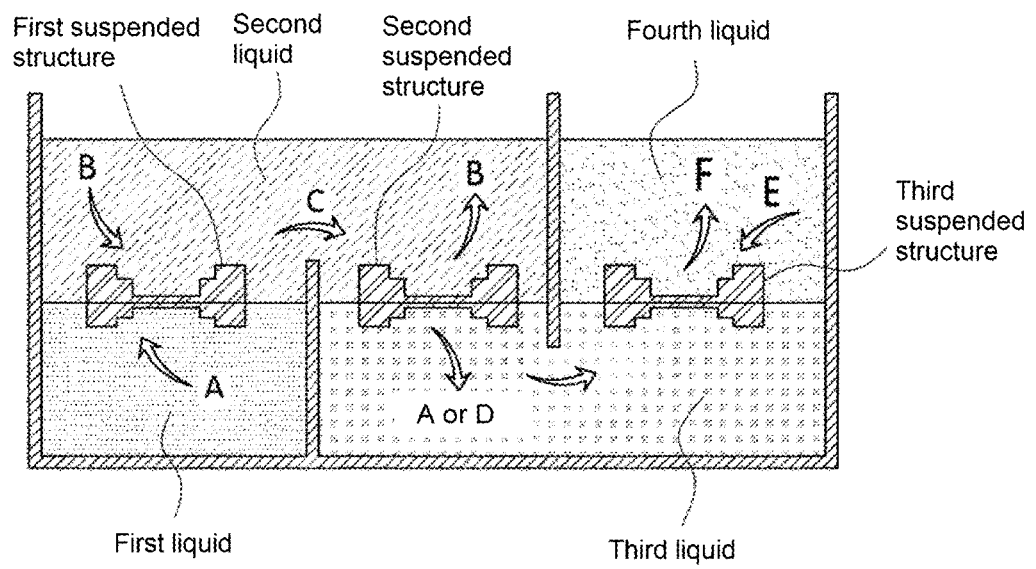
FIG. 17 is a schematic diagram illustrating an exemplary embodiment of a process of converting a reactant according to the present invention.

In addition, the process of converting a reactant at an interface between a liquid and a liquid according to the present invention, as shown in a schematic diagram of FIG. 17, may be performed under processing conditions in which a first liquid and a third liquid separated from each other are present in a lower part of a reaction container, a second liquid and a fourth liquid separated from each other are present in an upper part of the reaction container, and structures are present at each of an interface between the first liquid and the second liquid, an interface between the third liquid and the second liquid, an interface between the third liquid and the fourth liquid.

In this case, the first liquid and the second liquid have lower densities than that of the third liquid, and the second liquid has a lower density than that of the fourth liquid. However, the first liquid which does not come in direct contact with the fourth liquid does not need to have a lower density than that of the fourth liquid.

In addition, each of the structures (first to third structures) present at the interfaces may include different types of a first material.

A detailed description thereof will be provided as follows. A reactant A in the first liquid reacts with a reactant B in the second liquid by a first material of the first structure to form a product C, and then the product C in the second liquid forms a product A or a product D in the third liquid due to a first material in the second structure. Next, the product A or the product D in the third liquid reacts with a reactant E in the fourth liquid by a first material in the third structure to form a product F.

In addition, the first materials in the first to third structures may be the same or different first materials.

As such, the process of converting a reactant at an interface between a liquid and a liquid according to the present invention may vary depending on the type of liquids and the type of first materials.

Hereinafter, the present invention will be described according to the following embodiments. However, the following embodiments are merely presented to exemplify the present invention, and the scope of the present invention is not limited to the following embodiments.

EXAMPLES

Preparation Example 1: Preparation of Structure

An acrylonitrile butadiene styrene (ABS) polymer was used to prepare a structure shown in FIGS. 1 to 3. In this case, the structure had a hexagonal or spherical shape and was hollow.

Preparation Example 2: Preparation of Structure

Figure 18:
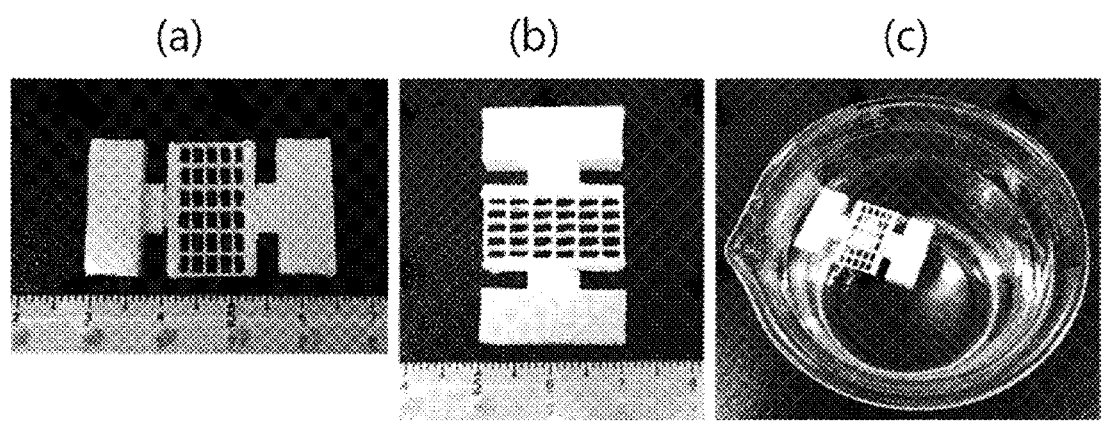
FIG. 18, in panels (a), (b) (c), shows images of a structure according to Preparation Example 2.

An ABS polymer was used to prepare two floating bodies and three platy structures in the form shown in FIG. 5, which were then assembled to prepare a structure composed of a three-layer support and two floating bodies shown in images of FIG. 18. In this case, the floating bodies of the structure were hollow.

The images of a structure prepared by assembling floating bodies and a body when a first material was not immobilized are shown in FIG. 18, in panels (a) and (b).

In addition, the image illustrating that the structure floats on water after a first material was applied is shown in FIG. 18, in panel (c).

Preparation Example 3: Preparation of Structure

A structure was prepared in the same manner as in Preparation Examples 1 and 2, except that a floating body having an empty void with a smaller volume than voids in the structure according to Preparation Example 1 and the floating body according to Preparation Example 2 was used.

Preparation Example 4: Preparation of Structure

A structure was prepared in the same manner as in Preparation Examples 1 and 2, except that a floating body having an empty void with a larger volume than voids in the structure according to Preparation Example 1 and the floating body according to Preparation Example 2 was used.

Preparation Example 5: Preparation of Polymer Nanofiber as Carrier

A polymer nanofiber was used as a carrier which immobilizes a carbonic anhydrase and a lipase. Polystyrene (PS; MW=950,400) and poly(styrene-co-maleic anhydride) (PSMA; MW=224,000) were used as the polymers for preparing the polymer nanofiber, and tetrahydrofuran (THF) and acetone were used as the organic solvents for dissolving the polymer. The polymer nanofiber was prepared using an electrospinning method. The electrospinning was performed using a syringe pump under a voltage operating condition of 7 kV at a flow rate of 0.1 ml/hr.

Preparation Example 6: Immobilization of First Material on Surface of Polymer Nanofiber In order to immobilize a carbonic anhydrase and a lipase, the above-prepared polymer nanofiber was mixed with a carbonic anhydrase solution (10 mg/ml; 50 mM sodium phosphate buffer (pH 7.6)). A container containing a carbonic anhydrase or lipase solution and the nanofiber was mixed for 30 minutes at 200 rpm, and then stirred at 4° C. for 2 hours to induce covalent bonding between the carbonic anhydrase and maleic anhydride which is a first functional group in the polymer nanofiber.

Next, in order to form a composite, 0.5% v/v glutaraldehyde as a cross-linking agent was added and ammonium sulfate as a settling agent was added so that the concentration of ammonium sulfate in the solution was 45% w/v, and then a reaction was induced in a refrigerator at 4° C. for 14 hours to easily form a composite. Afterward, a solution containing a composite was stirred using a 100 mM Tris buffer (pH 7.6) at 200 rpm for 30 minutes, and then washed with 100 mM PB. All enzyme-immobilized materials were stored at 4° C., thereby a composite shown in FIG. 3 was prepared.

Example 1

Water was added into an empty container, and then the structures according to Preparation Examples 1, 3, and 4 were introduced to identify a suspension degree of each structure, results of which are shown in FIG. 1.

Example 2

The carrier which immobilizes a carbonic anhydrase as a first material according to Preparation Example 5 was included in the body prepared in Preparation Example 1, and floating portions were coupled to both ends of the body to prepare a structure. Afterward, to a container having a size of 9 cm (diameter) and 22 cm (height) and equipped with a gas supply unit positioned at a height of 10 cm and having a diameter of 0.3 cm and a gas discharging unit facing the gas supply unit and having the same diameter as the gas supply unit, a Tris-HCl (pH 8.0) solution was added until a height of 5 cm was reached, and then the structure was positioned at a surface of the solution to prepare a reactor for converting carbon dioxide.

Comparative Example 1

Comparative Example 1 was implemented in the same manner as Example 2 except that a first material was not applied to a structure, and only the structure was allowed to float at an interface between a gas and a liquid.

Experimental Example 1: Collection of Carbon Dioxide and Conversion to Calcium Carbonate at Interface Between Gas and Liquid Carbon dioxide in a gaseous state was introduced through the gas supply unit of the reactor for converting carbon dioxide according to Example 2 at 200 mL/min for 20 minutes to induce a carbon dioxide conversion reaction. Afterward, 20 mL of a reaction solution was extracted and reacted with 10 mL of a 670 mM calcium chloride solution to precipitate a carbonate. In order to separate the carbonate thus precipitated, centrifugation was performed at 15,000 rpm for 15 minutes, and then a liquid portion was removed. The carbonate thus separated was dried in a 90° C. oven for 24 hours, and weight thereof was measured, results of which are shown in Table 1 below.

TABLE 1

|  | Example 2 | Comparative Example 1 |
| --- | --- | --- |
| Weight of converted calcium carbonate (mg) | 215 | 114 |

Referring to Table 1, it can be confirmed that a conversion reactor including a first material had a carbon dioxide conversion efficiency 1.9-fold higher than that in Comparative Example 1 in which a first material is not applied.

Example 3

A mixture of water and acid blue was prepared as a first solvent. Also, hexane was prepared as a second solvent.

Figure 19:
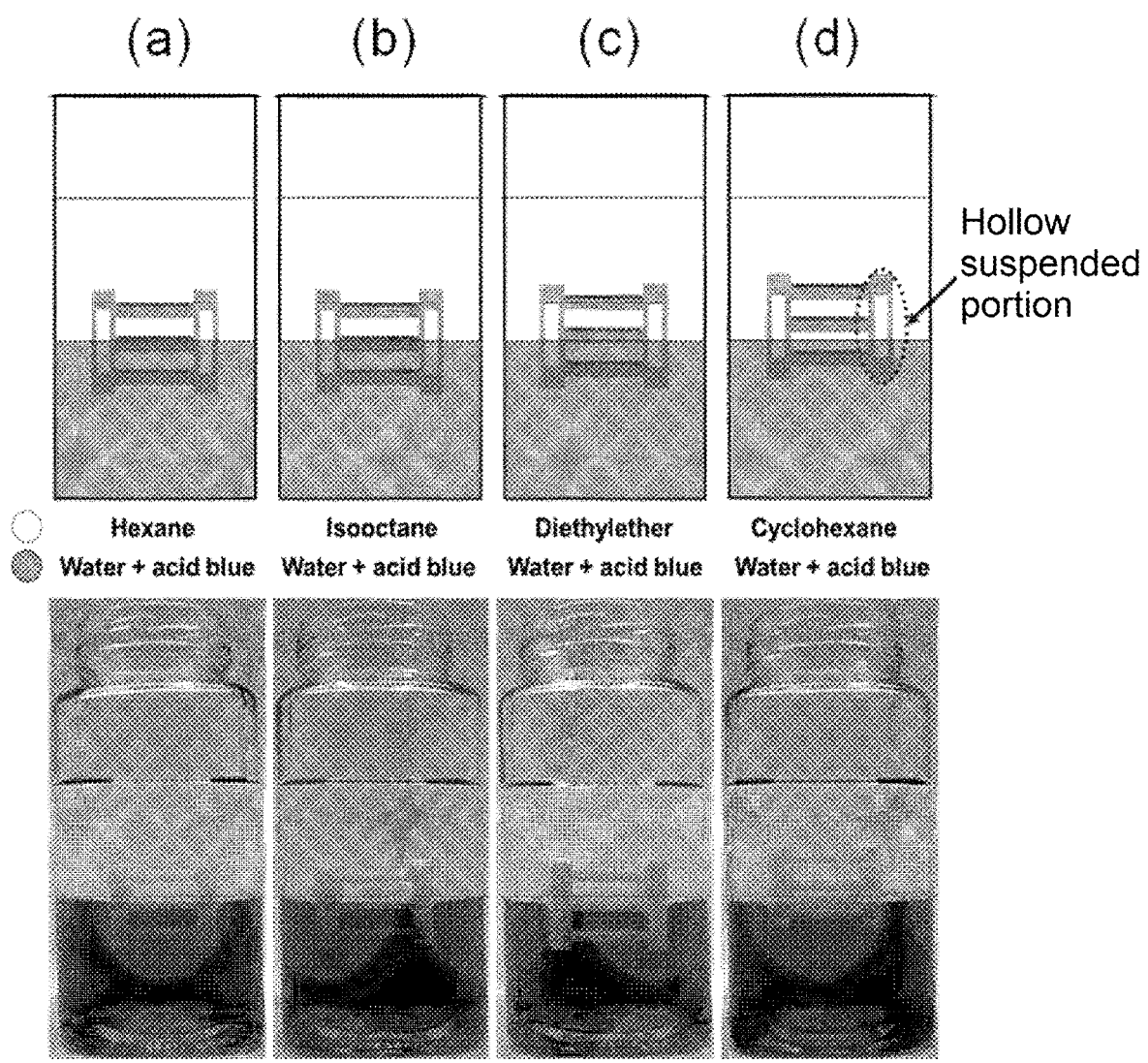
FIG. 19, in panels (a), (b), (c), and (d), shows images illustrating a measurement result of a suspension degree of each structure according to Examples 3 to 6 of the present invention.

Next, the first solvent was introduced into an empty container, and then the structure according to Preparation Example 2 was introduced. Afterward, the second solvent was introduced, and then a suspension degree of the structure was identified, the image of which is shown in FIG. 19, in panel (a).

Example 4

A mixture of water and acid blue was prepared as a first solvent. Also, isooctane was prepared as a second solvent.

Next, the first solvent was introduced into an empty container, and then the structure according to Preparation Example 2 was introduced. Afterward, the second solvent was introduced, and then a suspension degree of the structure was identified, the image of which is shown in FIG. 19, in panel (b).

Example 5

A mixture of water and acid blue was prepared as a first solvent. Also, diethyl ether was prepared as a second solvent.

Next, the first solvent was introduced into an empty container, and then the structure according to Preparation Example 2 was introduced. Afterward, the second solvent was introduced, and then a suspension degree of the structure was identified, the image of which is shown in FIG. 19, in panel (c).

Example 6

A mixture of water and acid blue was prepared as a first solvent. Also, cyclohexane was prepared as a second solvent.

Next, the first solvent was introduced into an empty container, and then the structure according to Preparation Example 2 was introduced. Afterward, the second solvent was introduced, and then a suspension degree of the structure was identified, the image of which is shown in FIG. 19, in panel (d).

Comparative Example 2

Comparative Example 2 was implemented in the same manner as Example 2 except that the structures according to Preparation Examples 3 and Preparation Example 4 were suspended at an interface between a first solvent and a second solvent.

Experimental Example 3: Evaluation of Suspension Degree of Structure at Interface Between Liquid and Liquid in Accordance with Solution In FIG. 19, panels (a), (b), (c), and (d) are images illustrating the testing of the structures according to Examples 3 to 6, respectively, and it can be confirmed that a suspension degree of a structure with respect to a first liquid varied in accordance with the type of solution of the second solvent.

It can be confirmed that this result is due to the fact that the densities of second liquids are different even though the structures according to Examples 3 to 6 have the same average density.

Experimental Example 4: Reaction Experiment at Interface Between Liquid and Liquid Material conversion reactions according to Example 2 and Comparative Example 1 were evaluated under a first liquid and a second liquid.

As the first liquid, a 10 mM 2-phenoxypropionic acid aqueous solution was prepared by dissolving 2-phenoxypropionic acid in a water solvent.

In addition, as the second liquid, a 1 M solution was prepared by dissolving butyl alcohol in isooctane.

Next, the structure according to Preparation Example 1 was suspended at an interface between a first solvent and a second solvent in Example 2, and a structure to which a first material was not applied was suspended in Comparative Example 1 to perform a reaction. Afterward, the concentration of butyl-2-phenoxypropanoate as a product was measured, the result of which is shown in FIG. 20.

Figure 20:
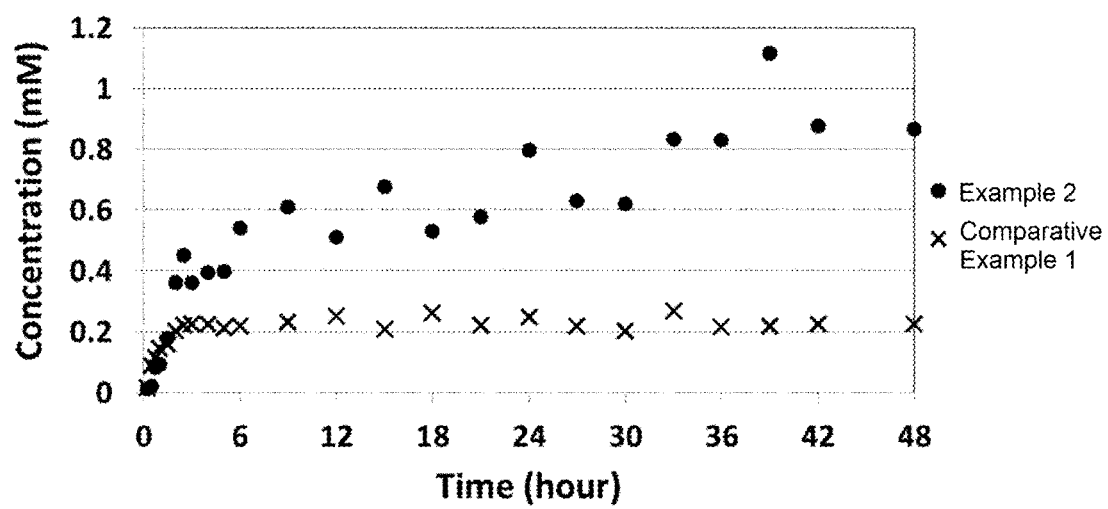
FIG. 20 is a graph illustrating a result of a reaction performed in Experimental Example 4.

Referring to FIG. 20, it can be confirmed that there is only a slight change in concentration of a product after about 4 hours had elapsed in the case of Comparative Example 1, whereas the concentration of a product was continuously increased over time in the case of Example 2.

Figure 21:
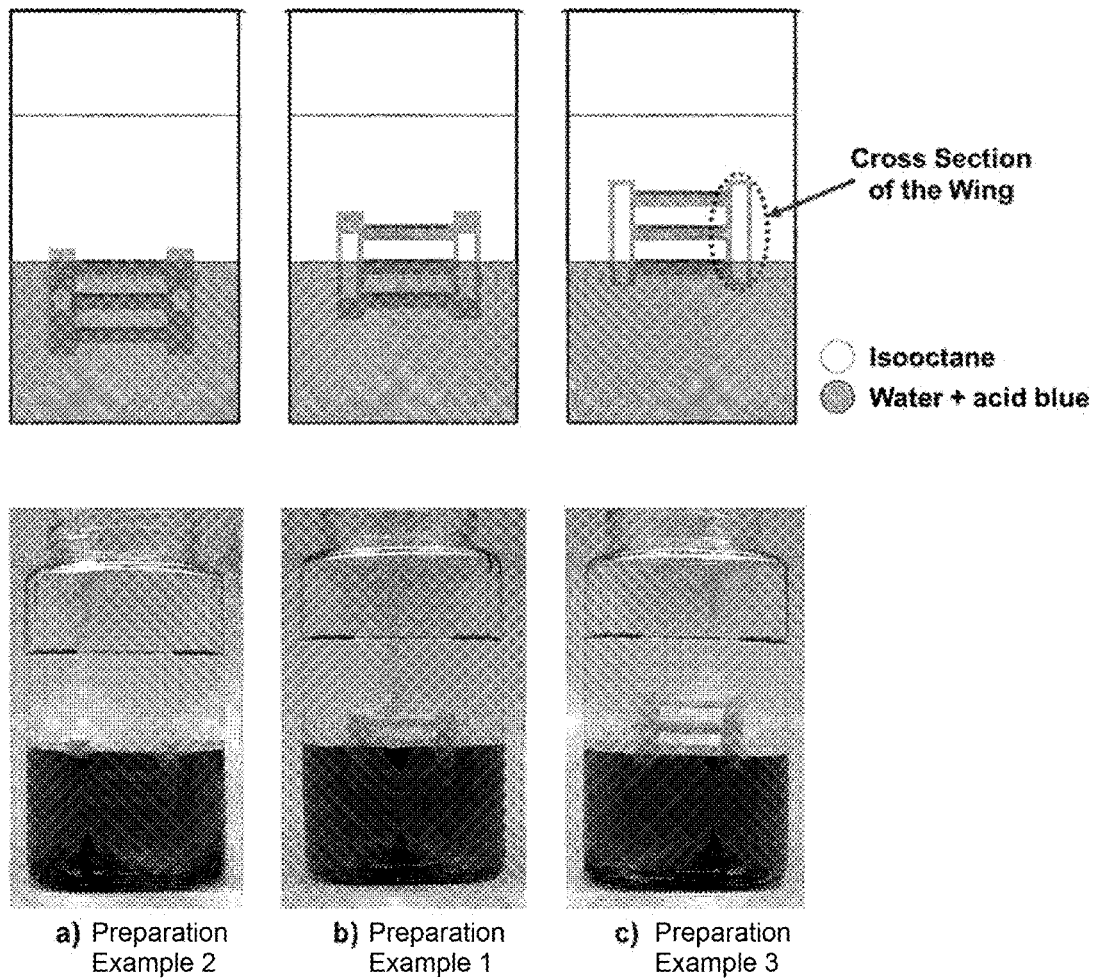
FIG. 21, in panels (a), (b), and (c), shows images illustrating that a suspension degree of a structure is adjusted by adjusting the size of a void in the suspended portion of a structure.

Experimental Example 5: Evaluation of Suspension Degree of Structure at Interface Between Liquid and Liquid in Accordance with Volume of Void In FIG. 21, panels (a), (b), and (c) are images illustrating the testing of structures according to Example 3 and Comparative Example 2, and it can be confirmed that a suspension degree of a structure with respect to a first liquid varied in accordance with the type of structure.

Meanwhile, referring to FIG. 5 through FIG. 21, while drawings and data obtained through experiments using the structure 1' according to the first embodiment and the structure 1 according to the second embodiment are disclosed, it is found that the same experiment and data can be obtained regardless of which one of the structure 1' according to the first embodiment and the structure 1 according to the second embodiment is used.

However, the user may select the structure 1' according to the first embodiment or the structure 1 according to the second embodiment for use as necessary.

Accordingly, the structure may prevent a product converted through a reaction at an interface between a liquid and a liquid from being reconverted to a reactant, and may also significantly improve the yield of a product by disposing a first material at an optimum position.

In addition, a large amount of a material present in a specific liquid may be separated and/or recovered. Also, the material may be synthesized through separation of an enantiomer and reactions at an interface.

Additionally, a structure may be positioned at an interface between a gas and a liquid, and may include a first material for easily combining with or converting a material present in a gas or liquid.

In addition, the structure includes a catalytic material and thus may be applied to collect and apply carbon dioxide, to decompose and remove oil present in a liquid, or to prevent or remove microorganism contamination.

Although the present invention has been described in detail with reference to exemplary embodiments of the present invention, the scope of the present invention is not limited to exemplary embodiments. It should be understood by those skilled in the art that other exemplary embodiments may be proposed by adding, modifying, and eliminating components and these exemplary embodiments may be included within the scope of the present invention.

The invention claimed is:

1. A structure comprising:
a support comprising at least two platy structures;
a density-adjusting body coupled to the support; and
a first material disposed between the platy structures,
wherein the density of the density-adjusting body is adjusted in accordance with a material of the density-adjusting body or a size of a void formed in the density-adjusting body, so that the platy structures and the first material can be positioned at an interface between a gas and a liquid or between a liquid and a liquid by adjusting the density of the density-adjusting body,
the platy structures have at least one opening which allows inflow and outflow of at least one reactant and at least one product.

2. The structure of claim 1, wherein the at least two platy structures have a mesh form.

3. The structure of claim 1, wherein the density-adjusting body comprises at least one void formed therein,
the void is filled with a second material, and
the second material includes one or more materials selected from the group consisting of air, nitrogen, oxygen, argon, carbon dioxide, neon, ozone, helium, methane, xenon, krypton, and hydrogen.

4. The structure of claim 1, wherein at least a portion of the density-adjusting body is made of at least one selected from acrylonitrile butadiene styrene, polythiophene, polylactic acid, polyvinyl alcohol, polycaprolactam, polycaprolactone, poly(lactic-co-glycolic acid), polyacrylonitrile, polyester, polyethylene, polyethyleneimine, polypropylene oxide, polyurethane, polyglycolic acid, polyethylene terephthalate, poly(methyl methacrylate), polystyrene, polydimethylsiloxane, poly(styrene-co-maleic anhydride), Teflon, collagen, nylon, cellulose, chitosan, glass, gold, silver, aluminum, iron, copper, and silicon.

5. The structure of claim 1, wherein the first material is combined with the platy structures by adsorption, ionic bonding, covalent bonding, or via an adhesive material.

6. The structure of claim 1, wherein the first material is combined with a carrier by adsorption, ionic bonding, covalent bonding, or via an adhesive material, and
the carrier with the first material is combined with a surface of the platy structures by adsorption, ionic bonding, covalent bonding, or via an adhesive material, or embedded in the platy structures.

7. The structure of claim 6, wherein the carrier includes at least one selected from polymer fibers, porous particles, carbon tubes, polymer tubes, wires, pillars, graphene, fullerenes, polynorepinephrine, and spherical particles.

8. The structure of claim 1, wherein the first material includes at least one selected from an organic catalyst, an inorganic catalyst, a biomolecule, and a microorganism.

9. The structure of claim 8, wherein the first material includes the organic catalyst, the organic catalyst forms an aggregate via cross-linking between organic catalysts by using a cross-linking agent, and
the cross-linking agent includes one or more selected from the group consisting of diisocyanate, dianhydride, diepoxide, dialdehyde, diimide, 1-ethyl-3-dimethylaminopropyl carbodiimide, glutaraldehyde, bis(imidoester), bis(succinimidyl ester), diacid chloride, dopamine, a compound containing a dopamine-derived catechol group, genipin, and ethylene glycol diglycidyl ether.

10. The structure of claim 8, wherein the first material includes the organic catalyst, the organic catalyst settles by a settling agent and forms an aggregate via cross-linking between organic catalysts by using a cross-linking agent,
the cross-linking agent includes one or more selected from the group consisting of diisocyanate, dianhydride, diepoxide, dialdehyde, diimide, 1-ethyl-3-dimethylaminopropyl carbodiimide, glutaraldehyde, bis(imidoester), bis(succinimidyl ester), diacid chloride, dopamine, a compound containing a dopamine-derived catechol group, genipin, and ethylene glycol diglycidyl ether, and
the settling agent includes one or more selected from the group consisting of methanol, ethanol, 1-propanol, 2-propanol, butyl alcohol, acetone, polyethylene glycol, ammonium sulfate, sodium chloride, sodium sulfate, sodium phosphate, potassium chloride, potassium sulfate, potassium phosphate, and an aqueous solution thereof.

11. The structure of claim 8, wherein the organic catalyst includes one or more selected from the group consisting of carbonic anhydrases, glucose oxidases, trypsin, chymotrypsin, subtilisin, papain, thermolysin, lipases, peroxidases, acylases, lactonase, proteases, tyrosinase, laccases, cellulases, xylanases, organophosphohydrolase, cholinesterases, formate dehydrogenases, aldehyde dehydrogenases, alcohol dehydrogenases, glucose dehydrogenases, and glucose isomerase,
the inorganic catalyst includes one or more selected from the group consisting of platinum, rhodium, palladium, lead, iridium, rubidium, iron, nickel, zinc, cobalt, copper, manganese, titanium, ruthenium, silver, molybdenum, tungsten, aluminum, antimony, tin, bismuth, barium, osmium, nitrogen oxide, copper oxide, manganese oxide, titanium oxide, vanadium oxide, and zinc oxide, the biomolecule includes one or more selected from the group consisting of albumin, insulin, collagen, an antibody, an antigen, protein A, protein G, avidin, streptavidin, biotin, a nucleic acid, a peptide, a lectin, and a carbohydrate, and the microorganism includes one or more selected from the group consisting of *Bacillus subtilis, Bacillus licheniformis, Bacillus polyfermenticus, Bacillus mesentericus, Saccharomyces cerevisiae, Clostridium butyricum, Streptococcus faecalis, Streptococcus faecium, Micrococcus caseolyticus, Staphylococcus aureus, Lactobacillus casei, Lactobacillus plantarum, Leuconostoc mesenteroides, Debaryomyces nicotianae, Acinetobacter calcoaceticus, Alcaligenes odorans, Aromatoleum aromaticum, Geobacter metallireducens, Dechloromonas aromatic, Arthrobacter* sp., and *Alcanivorax borkumensis*.

\* \* \* \* \*